(12) United States Patent
Mahmoudi

(10) Patent No.: US 12,376,879 B2
(45) Date of Patent: Aug. 5, 2025

(54) EXPANDABLE ELEMENTS FOR SHUNTING CATHETERS

(71) Applicant: THERAHEART INC., Irvine, CA (US)

(72) Inventor: Rani Abdullah Mahmoudi, Huntington Beach, CA (US)

(73) Assignee: THERAHEART INC., Irvine, CA (US)

( * ) Notice: Subject to any disclaimer, the term of this patent is extended or adjusted under 35 U.S.C. 154(b) by 0 days.

(21) Appl. No.: 18/593,835

(22) Filed: Mar. 1, 2024

(65) Prior Publication Data

US 2024/0293148 A1    Sep. 5, 2024

Related U.S. Application Data

(60) Provisional application No. 63/558,028, filed on Feb. 26, 2024, provisional application No. 63/449,878, filed on Mar. 3, 2023.

(51) Int. Cl.
*A61B 90/00* (2016.01)
*A61B 17/00* (2006.01)
(Continued)

(52) U.S. Cl.
CPC .... *A61B 17/3403* (2013.01); *A61B 17/00234* (2013.01); *A61B 34/20* (2016.02); *A61B 90/39* (2016.02); *A61B 2017/00199* (2013.01); *A61B 2017/00252* (2013.01); *A61B 2017/00305* (2013.01); *A61B 2017/00411* (2013.01);
(Continued)

(58) Field of Classification Search
USPC .................................. 607/115–116, 119, 122
See application file for complete search history.

(56) References Cited

U.S. PATENT DOCUMENTS

| 4,861,336 A | 8/1989 | Helzel |
| 5,255,679 A | 10/1993 | Imran |
| (Continued) | | |

FOREIGN PATENT DOCUMENTS

| CA | 2472701 C | 11/2012 |
| CN | 109965974 A | 7/2019 |
| (Continued) | | |

OTHER PUBLICATIONS

Babaliaros et al., "Emerging Applications for Transseptal Left Heart Catheterization: Old Techniques for New Procedures," J. Am. Coll..Cardiol., 2008; 51:2116-22.
(Continued)

*Primary Examiner* — Jennifer Pitrak McDonald
*Assistant Examiner* — Michael T. Holtzclaw
(74) *Attorney, Agent, or Firm* — Faegre Drinker Biddle & Reath LLP

(57) ABSTRACT

At least some embodiments of the present disclosure are directed to systems and methods for creating a shunt in a patient. In some embodiments, a shunting catheter includes a catheter shaft having a distal end and a proximal end, the catheter shaft including a shaft lumen; a balloon shaft disposed in the shaft lumen at a first state and extended from the catheter shaft at a second state; a balloon element disposed on the balloon shaft and expandable at the second state; and at least one electrode of one or more electrodes disposed on the balloon element.

21 Claims, 22 Drawing Sheets

(51) Int. Cl.
  *A61B 17/34* (2006.01)
  *A61B 34/20* (2016.01)
(52) U.S. Cl.
  CPC .............. *A61B 2017/00544* (2013.01); *A61B 2017/00557* (2013.01); *A61B 2034/2046* (2016.02); *A61B 2090/3966* (2016.02)

(56) References Cited

U.S. PATENT DOCUMENTS

| | | |
|---|---|---|
| 5,328,472 A | 7/1994 | Rupp et al. |
| 5,800,450 A | 9/1998 | Lary et al. |
| 6,179,832 B1 | 1/2001 | Tartaglia et al. |
| 6,726,677 B1 | 4/2004 | Flaherty et al. |
| 7,018,400 B2 | 3/2006 | Haarstad et al. |
| 7,150,745 B2 | 12/2006 | Stern et al. |
| 7,655,005 B2 | 2/2010 | Bhola |
| 7,674,256 B2 | 3/2010 | Marrouche et al. |
| 7,966,057 B2 | 6/2011 | Macaulay et al. |
| 8,021,359 B2 | 9/2011 | Auth et al. |
| 8,043,360 B2 | 10/2011 | McNamara et al. |
| 8,157,860 B2 | 4/2012 | McNamara et al. |
| 8,172,896 B2 | 5/2012 | McNamara et al. |
| 8,214,015 B2 | 7/2012 | Macaulay et al. |
| 8,226,619 B2 | 7/2012 | Smith et al. |
| 8,252,042 B2 | 8/2012 | McNamara et al. |
| 8,374,680 B2 | 2/2013 | Thompson |
| 8,585,596 B1 | 11/2013 | Flaherty et al. |
| 8,617,152 B2 | 12/2013 | Flaherty et al. |
| 8,728,073 B2 | 5/2014 | McDaniel |
| 8,758,363 B2 | 6/2014 | Nishtala et al. |
| 8,874,237 B2 | 10/2014 | Schilling |
| 8,882,697 B2 | 11/2014 | McNamara et al. |
| 8,900,250 B2 | 12/2014 | Fritscher-Ravens et al. |
| 8,926,602 B2 | 1/2015 | Pageard |
| 8,968,233 B2 | 3/2015 | Duffy et al. |
| 9,089,314 B2 | 7/2015 | Wittenberger |
| 9,345,858 B2 | 5/2016 | Flaherty et al. |
| 9,468,744 B2 | 10/2016 | Arana et al. |
| 9,642,993 B2 | 5/2017 | McNamara et al. |
| 9,789,294 B2 | 10/2017 | Taft et al. |
| 9,808,303 B2 | 11/2017 | Gelfand et al. |
| 9,808,304 B2 | 11/2017 | Lalonde |
| 9,814,483 B2 | 11/2017 | Vardi |
| 9,918,789 B2 | 3/2018 | Bagley et al. |
| 10,016,620 B2 | 7/2018 | Aljuri et al. |
| 10,039,905 B1 | 8/2018 | Taft et al. |
| 10,154,878 B2 | 12/2018 | Greenlaw et al. |
| 10,188,375 B2 | 1/2019 | McNamara et al. |
| 10,207,126 B2 | 2/2019 | Benson |
| 10,245,352 B2 | 4/2019 | Wilson et al. |
| 10,327,791 B2 | 6/2019 | Argentine et al. |
| 10,426,497 B2 | 10/2019 | Chou et al. |
| 10,449,339 B2 | 10/2019 | Wilson et al. |
| 10,568,686 B2 * | 2/2020 | Lee ................. A61B 5/6853 |
| 10,568,688 B2 | 2/2020 | Hu et al. |
| 10,568,751 B2 | 2/2020 | McNamara |
| 10,624,621 B2 | 4/2020 | Celermajer |
| 10,639,060 B2 | 5/2020 | Vardi et al. |
| 10,722,300 B2 | 7/2020 | Gupta et al. |
| 10,729,492 B2 | 8/2020 | Brown et al. |
| 10,758,714 B2 | 9/2020 | Laby et al. |
| 10,842,562 B2 | 11/2020 | Zhang et al. |
| 10,857,328 B2 | 12/2020 | Walzman |
| 10,864,041 B2 | 12/2020 | Urbanski et al. |
| 10,932,723 B2 | 3/2021 | Eliason et al. |
| 10,980,552 B2 | 4/2021 | Mustapha |
| 10,987,494 B2 | 4/2021 | Skinner et al. |
| 10,993,735 B2 | 5/2021 | Vardi et al. |
| 10,993,736 B2 | 5/2021 | Vardi et al. |
| 11,052,246 B2 | 7/2021 | Stewart et al. |
| 11,065,019 B1 | 7/2021 | Chou et al. |
| 11,071,585 B2 | 7/2021 | Zhang et al. |
| 11,083,520 B2 | 8/2021 | Ghaly et al. |
| 11,135,410 B2 | 10/2021 | Finch et al. |
| 11,224,449 B2 | 1/2022 | Chou et al. |
| 11,224,450 B2 | 1/2022 | Chou et al. |
| 11,266,817 B2 * | 3/2022 | Cope ................. A61M 25/1011 |
| 11,350,990 B2 | 6/2022 | Gupta et al. |
| 11,369,346 B2 | 6/2022 | Stigall et al. |
| 11,369,405 B2 | 6/2022 | Vardi et al. |
| 11,399,852 B2 | 8/2022 | Wilson et al. |
| 11,534,239 B2 | 12/2022 | Bishara et al. |
| 11,612,432 B2 | 3/2023 | Pate et al. |
| 11,648,042 B2 | 5/2023 | Kelley |
| 11,690,609 B2 | 7/2023 | Celermajer |
| 11,717,429 B2 | 8/2023 | Schwartz et al. |
| 11,752,314 B2 | 9/2023 | Taft et al. |
| 11,793,529 B2 | 10/2023 | Chou et al. |
| 11,806,032 B2 | 11/2023 | Chou et al. |
| 11,865,282 B2 | 1/2024 | Nae et al. |
| 11,957,374 B2 | 4/2024 | Vardi et al. |
| 12,004,802 B2 | 6/2024 | Scott et al. |
| 2005/0154386 A1 | 7/2005 | West et al. |
| 2005/0171527 A1 | 8/2005 | Bhola |
| 2006/0135961 A1 | 6/2006 | Rosenman et al. |
| 2007/0083194 A1 | 4/2007 | Kunis et al. |
| 2009/0125097 A1 | 5/2009 | Bruszewski et al. |
| 2012/0123466 A1 | 5/2012 | Porter et al. |
| 2012/0130417 A1 | 5/2012 | Lepulu et al. |
| 2014/0277054 A1 | 9/2014 | McNamara et al. |
| 2015/0209526 A1 | 7/2015 | Matsubara et al. |
| 2016/0175041 A1 | 6/2016 | Govari et al. |
| 2017/0072173 A1 * | 3/2017 | Van Dam ............ A61B 17/1114 |
| 2018/0236211 A1 | 8/2018 | Henschel |
| 2019/0374254 A1 | 12/2019 | Arevalos et al. |
| 2020/0030588 A1 | 1/2020 | Heilman et al. |
| 2020/0038672 A1 | 2/2020 | Satake |
| 2020/0170662 A1 | 6/2020 | Vardi et al. |
| 2020/0238059 A1 | 7/2020 | Wang et al. |
| 2020/0261704 A1 | 8/2020 | Wang et al. |
| 2020/0367924 A1 | 11/2020 | Lenker et al. |
| 2021/0038298 A1 | 2/2021 | Scott et al. |
| 2021/0045805 A1 | 2/2021 | Govari et al. |
| 2021/0085384 A1 | 3/2021 | Morey et al. |
| 2021/0128229 A1 * | 5/2021 | Panescu ............... A61B 5/4041 |
| 2021/0196373 A1 | 7/2021 | He et al. |
| 2021/0228227 A1 | 7/2021 | Vardi et al. |
| 2021/0315629 A1 | 10/2021 | Yang et al. |
| 2021/0369321 A1 | 12/2021 | Yang et al. |
| 2021/0393324 A1 | 12/2021 | Moriyama et al. |
| 2021/0401494 A1 * | 12/2021 | Passman ................ A61B 17/11 |
| 2022/0022954 A1 | 1/2022 | Shuros et al. |
| 2022/0110679 A1 | 4/2022 | Wang et al. |
| 2022/0249160 A1 | 8/2022 | Pate et al. |
| 2022/0257318 A1 | 8/2022 | Belalcazar |
| 2022/0265346 A1 | 8/2022 | Gupta et al. |
| 2022/0273279 A1 | 9/2022 | Valdez et al. |
| 2022/0330975 A1 | 10/2022 | Rafiee et al. |
| 2023/0041021 A1 | 2/2023 | Urbanski et al. |
| 2023/0078647 A1 | 3/2023 | Sharma et al. |
| 2023/0099410 A1 * | 3/2023 | Primeaux .......... A61B 18/1477 606/41 |
| 2023/0210592 A1 | 7/2023 | Agnew et al. |
| 2023/0248425 A1 | 8/2023 | Iijima |
| 2023/0270491 A1 | 8/2023 | Mori et al. |
| 2023/0293877 A1 | 9/2023 | Hoem |
| 2024/0050717 A1 | 2/2024 | Rickerson et al. |

FOREIGN PATENT DOCUMENTS

| | | |
|---|---|---|
| CN | 115475001 A | 12/2022 |
| CN | 115590605 A | 1/2023 |
| EP | 1878453 B1 | 12/2014 |
| EP | 3238646 A2 | 11/2017 |
| EP | 3705154 A1 | 9/2020 |
| JP | 5237572 B2 | 7/2013 |
| WO | 2003/049643 A1 | 6/2003 |
| WO | 2018/229768 A2 | 12/2018 |
| WO | 2018/229768 A9 | 12/2018 |
| WO | 2020/024612 A1 | 2/2020 |
| WO | 2020/232384 A1 | 11/2020 |
| WO | 2020/242491 A1 | 12/2020 |
| WO | 2021/091566 A1 | 5/2021 |
| WO | 2021/190547 A1 | 9/2021 |

(56) References Cited

FOREIGN PATENT DOCUMENTS

| WO | 2022/113054 A1 | 6/2022 |
|---|---|---|
| WO | 2022/135375 A1 | 6/2022 |
| WO | 2022/166973 A1 | 8/2022 |
| WO | 2022/246158 A1 | 11/2022 |
| WO | 2023/088572 A1 | 5/2023 |

OTHER PUBLICATIONS

Edwards Lifesciences, "The Alt-Flow II trial for heart failure," 10 pages (undated).

Tanaka et al., "Treatment of Hepatic Encephalopathy Due to Inferior Mesenteric Vein/Inferior Vena Cava and Gonadal Vein Shunt Using Dual Balloon-Occluded Retrograde Transvenous Obliteration," Cardiovasc Intervent Radiol, 2009, 32:390-393 (published online Oct. 7, 2008).

United States Patent and Trademark Office, Office Action mailed Jun. 20, 2024, for U.S. Appl. No. 18/623,954.

United States Patent and Trademark Office, Office Action mailed May 17, 2024, for U.S. Appl. No. 18/624,014.

Wilson et al., "Successful Tanscatheter Occlusion of an Anomalous Pulmonary Vein With Dual Drainage to the Left Atrium," Catheter Cardiovasc Interv, 2015, 85:1212-1216 (published online in Wiley Online Library, Apr. 7, 2015).

Patent Cooperative Treaty, International Search Report, mailed Jul. 17, 2024, in PCT/US2024/022547.

Patent Cooperative Treaty, International Search Report, mailed Jul. 25, 2024, in PCT/US2024/023345.

Patent Cooperative Treaty, International Search Report, mailed Jun. 24, 2024, in PCT/US2024/018244.

Patent Cooperative Treaty, Written Opinion, mailed Jul. 17, 2024, in PCT/US2024/022547.

Patent Cooperative Treaty, Written Opinion, mailed Jul. 25, 2024, in PCT/US2024/023345.

Patent Cooperative Treaty, Written Opinion, mailed Jun. 24, 2024, in PCT/US2024/018244.

United States Patent and Trademark Office, Office Action mailed Jul. 12, 2024, for U.S. Appl. No. 18/593,832.

\* cited by examiner

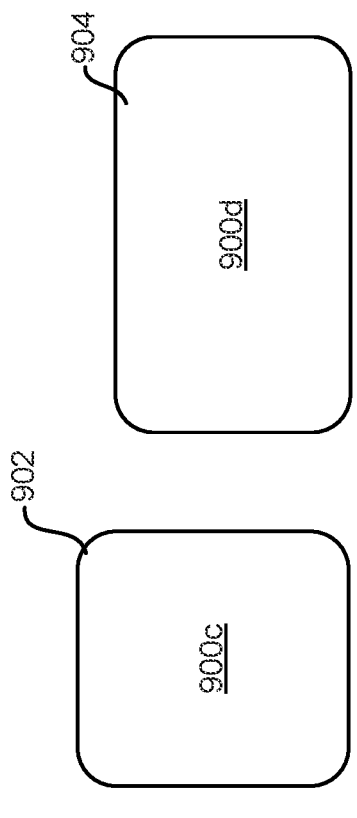
FIG. 9D
FIG. 9C
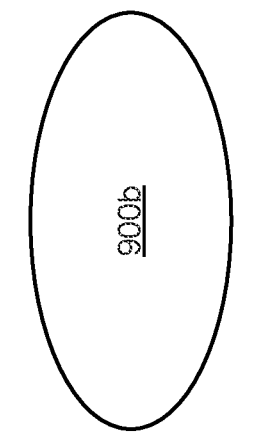
FIG. 9B
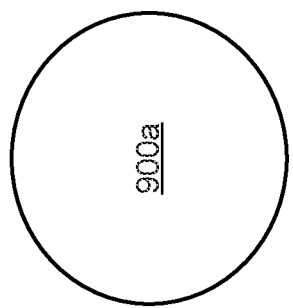
FIG. 9A

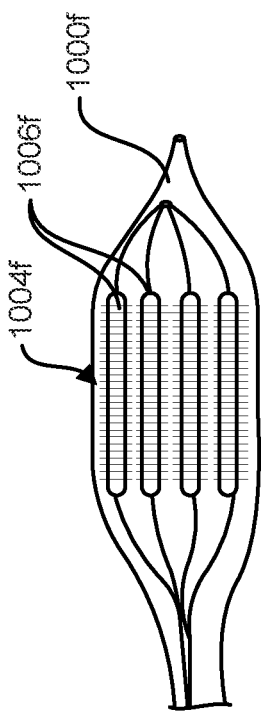
FIG. 10E
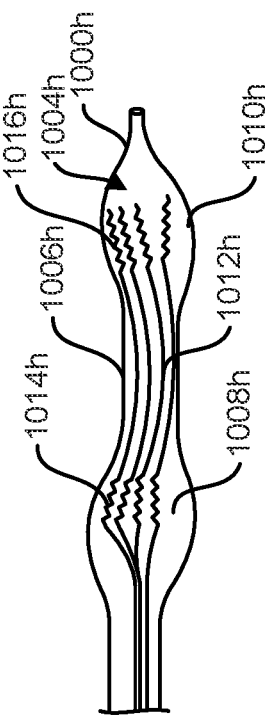
FIG. 10F
FIG. 10G
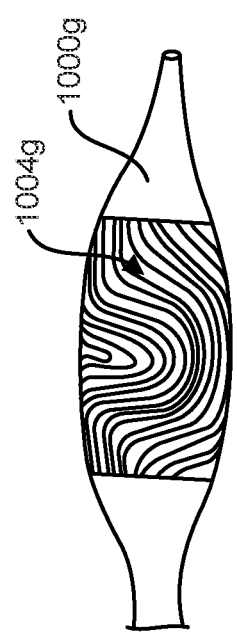
FIG. 10H

EXPANDABLE ELEMENTS FOR SHUNTING CATHETERS

CROSS REFERENCE TO RELATED APPLICATIONS

This application claims priority to U.S. Provisional Application No. 63/449,878, filed on Mar. 3, 2023, and U.S. Provisional Application No. 63/558,028, filed on Feb. 26, 2024, all of which are incorporated by reference herein for all purposes.

FIELD

Certain embodiments of the present disclosure relate to medical systems, apparatus, and methods for creating a shunt in a patient. More specifically, some embodiments of the present disclosure relate to medical systems, apparatus, and methods for creating a shunt on a cardiovascular system wall in a patient.

BACKGROUND

Heart failure is a serious condition that happens when a heart cannot pump enough blood and oxygen to support other organs in your body. Heart failure is classified according to left ventricular (LV) function as "heart failure with reduced ejection fraction (EF)" (HFrEF; EF<40%), "mid-range EF" (HFmrEF; EF 40-49%), or "preserved EF" (HFpEF; EF≥50%). About half the patients with heart failure have HFpEF. HFpEF generally happens when LV and left atrial filling pressures increase significantly during exercise, with an associated increase in pulmonary pressures leading to pulmonary congestion. Structural interventions to lower elevated either left or right atrial filling pressures are gaining attention.

Studies in heart failure show that lowering left atrial pressure may reduce cardiovascular events while improving functional capacity. The creation of an interatrial shunt has emerged as a therapy to decompress the left atrium in patients with acute and chronic left HF. As such, attention has turned toward the development of interatrial shunt devices (IASDs) as a means of reducing the detrimental increase in left-sided filling pressures with exercise in an effort to improve symptomatology. The IASDs may be used to treat various kinds of heart failure and/or other diseases that may result in too high of a pressure in the right atrium of a patient.

SUMMARY

Current IASDs reside in the interatrial septum, with risk for right-to-left shunting and systemic embolization. Moreover, preservation of the interatrial septum is important with an increasing number of left-sided transseptal transcatheter interventions. Ways to improve IASDs for safer and better procedures are needed.

According to some embodiments, shunting catheter includes a catheter shaft having a distal end and a proximal end, the catheter shaft including a shaft lumen; a balloon shaft disposed in the shaft lumen at a first state and extended from the catheter shaft at a second state; a balloon element disposed on the balloon shaft and expandable at the second state; and at least one electrode of one or more electrodes disposed on the balloon element.

In some embodiments, the catheter shaft defines a first axis; wherein the balloon shaft defines a second axis at the second state; wherein the second axis and the first axis form an angle greater than zero degree. In certain embodiments, the balloon element has a balloon length along the second axis and a balloon width perpendicular to the second axis; wherein the balloon length is greater than the balloon width when the balloon element is inflated. In some embodiments, the balloon element has a balloon length along the second axis and a balloon width perpendicular to the second axis; wherein the balloon length is smaller than the balloon width when the balloon element is inflated. In certain embodiments, the balloon element has a diameter in a range of three millimeters to fifteen millimeters when the balloon element is inflated.

In some embodiments, the balloon element has a first inflated state and a second inflated state; wherein the balloon element has a first balloon diameter at the first inflated state; wherein the balloon element has a second balloon diameter at the second inflated state; wherein the first balloon diameter is different from the second balloon diameter.

In certain embodiments, the balloon element includes a first inflatable portion having a first balloon diameter and a second inflatable portion having a second balloon diameter when the balloon element is inflated; wherein the first balloon diameter is different from the second balloon diameter.

In some embodiments, the balloon element includes a narrow section in a middle of the balloon element; wherein the balloon element includes a first section at a distal end of the balloon element and a second section at a proximal end of the balloon element; wherein the narrow section is between the first section and the second section; wherein the narrow section has a diameter smaller than a diameter of the first section or a diameter of the second section. In certain embodiments, the balloon element has a cross-sectional shape perpendicular to the second axis; wherein the cross-section shape is circular, oval or rectangular. In some embodiments, the balloon element includes an anchor component configured to facilitate a placement of the balloon element within a patient, and a shunting component mechanically coupled to the anchor component.

In certain embodiments, the anchor component has a first diameter, wherein the shunting component has a second diameter, and wherein the first diameter is larger than the second diameter. In some embodiments, the at least one electrode of the one or more electrodes is disposed on the shunting component of the balloon element. In certain embodiments, the anchor component and the shunting component share an interior lumen.

In some embodiments, the anchor component is a first balloon and the shunting component is a second balloon that does not share lumen with the first balloon. In certain embodiments, the anchor component is configured to be inflated to a first inflated state and the shunting component is configured to remain deflated at the first inflated state, wherein the anchor component is configured to be inflated to a second inflated state and the shunting component is configured to remain deflated at the second inflated state. In some embodiments, the anchor component is configured to pull back a tissue wall at the first inflated state.

In certain embodiments, the balloon element is folded into a plurality of pleats at the first state, and wherein a first electrode of the one or more electrodes is disposed entirely on a pleating surface on one side of one of the plurality of pleats. In some embodiments, the at least one electrode of the one or more electrodes has a center portion and a plurality of protrusions extended from the center portion, wherein at least a part of the plurality of protrusions are parallel. In certain embodiments, the anchor component has a proximal surface defining a plane angled relative to a longitudinal axis of the balloon element.

According to certain embodiments, a shunting catheter system includes a shunting catheter including: a catheter shaft having a distal end and a proximal end, the catheter shaft including a shaft lumen; a shunting element disposed in the shaft lumen at a first state and extended from the catheter shaft at a second state; and an apposition element disposed proximate to the shunting element, the apposition element being protruded from the catheter shaft at the second state. In some embodiments, the shunting catheter system further includes an energy source connected to the shunting catheter; and a controller connected to the energy source including one or more processors; wherein the one or more processors are configured to control the energy source to deliver energy to the shunting catheter.

In some embodiments, the shunting catheter system further includes an imaging device including: one or more visualization elements disposed proximate the shunting element for determining a location of the shunting element within a heart of a patient, and a display for visualizing the location.

According to some embodiments, a method for creating a shunt includes deploying a shunting catheter in a first state, the shunting catheter including: a catheter shaft having a distal end and a proximal end, the catheter shaft including a shaft lumen; a shunting element having a proximal end and a distal end, wherein the shunting element is disposed in the shaft lumen at the first state; and a puncture element disposed proximate to the distal end of the shunting element; disposing the shunting catheter approximate to a target location of a patient; operating the shunting catheter to a second state, wherein the shunting element extends from the catheter shaft at an angle greater than zero degree at the proximal end of the shunting element at the second state; puncturing, using the puncture element, an opening at the target location; and expanding the opening using the shunting element.

In certain embodiments, the shunting element includes an expandable element disposed at the distal end of the shunting element; wherein the expandable element has a plurality of states, and wherein the plurality of states of the expandable element includes a compressed state, a first inflated state, and a second inflated state.

In some embodiments, the method further includes treating tissue surrounding the opening using the expandable element at the first inflated state or the second inflated state. In certain embodiments, the method further includes determining a location of the shunting element using an imaging device; wherein the imaging device includes one or more visualization elements disposed proximate the shunting element. In some embodiments, the method further includes deploying the shunting catheter in the first state includes inserting the shunting catheter through a superior vena cava or an inferior vena cava of the patient into a coronary sinus of the patient.

In certain embodiments, the method further includes removing the shunting catheter from the patient. In some embodiments, the method further includes generating the shunt using the shunting element; wherein the shunt includes the opening between a coronary sinus and a left atrium of the patient. In certain embodiments, the shunting element includes an expandable element disposed at the distal end of the shunting element. In some embodiments, the expandable element includes an anchor component and a shunting element. In certain embodiments, the expandable element has a plurality of states including a compressed state, a first inflated state, and a second inflated state.

In some embodiments, the expanding the opening using the shunting element includes: disposing the anchor component distal of the target location; expanding the anchor component at the first inflated state to position the expandable element; and expanding the shunting component at the second inflated state.

According to some embodiments, a shunting catheter includes a catheter shaft having a distal end and a proximal end, the catheter shaft including a shaft lumen; a balloon shaft disposed in the shaft lumen at a first state and extended from the catheter shaft at a second state; and a balloon element disposed on the balloon shaft and configured to be expandable at the second state; wherein the balloon element includes an anchor component and a shunting component, the anchor component is configured to position the balloon element at the target location of the patient, and the shunting component has a diameter smaller than a diameter of the anchor component when both the anchor component and the shunting component are inflated; wherein the shunting component is configured to deliver ablation energy to the target location of the patient.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 9A-D are examples of cross-section views of a balloon element, in accordance with embodiments of the present disclosure.

FIGS. 10A-I are schematic diagrams of examples of electrode configurations placed on a balloon element, according to certain embodiments of the present disclosure.

Figure 1:
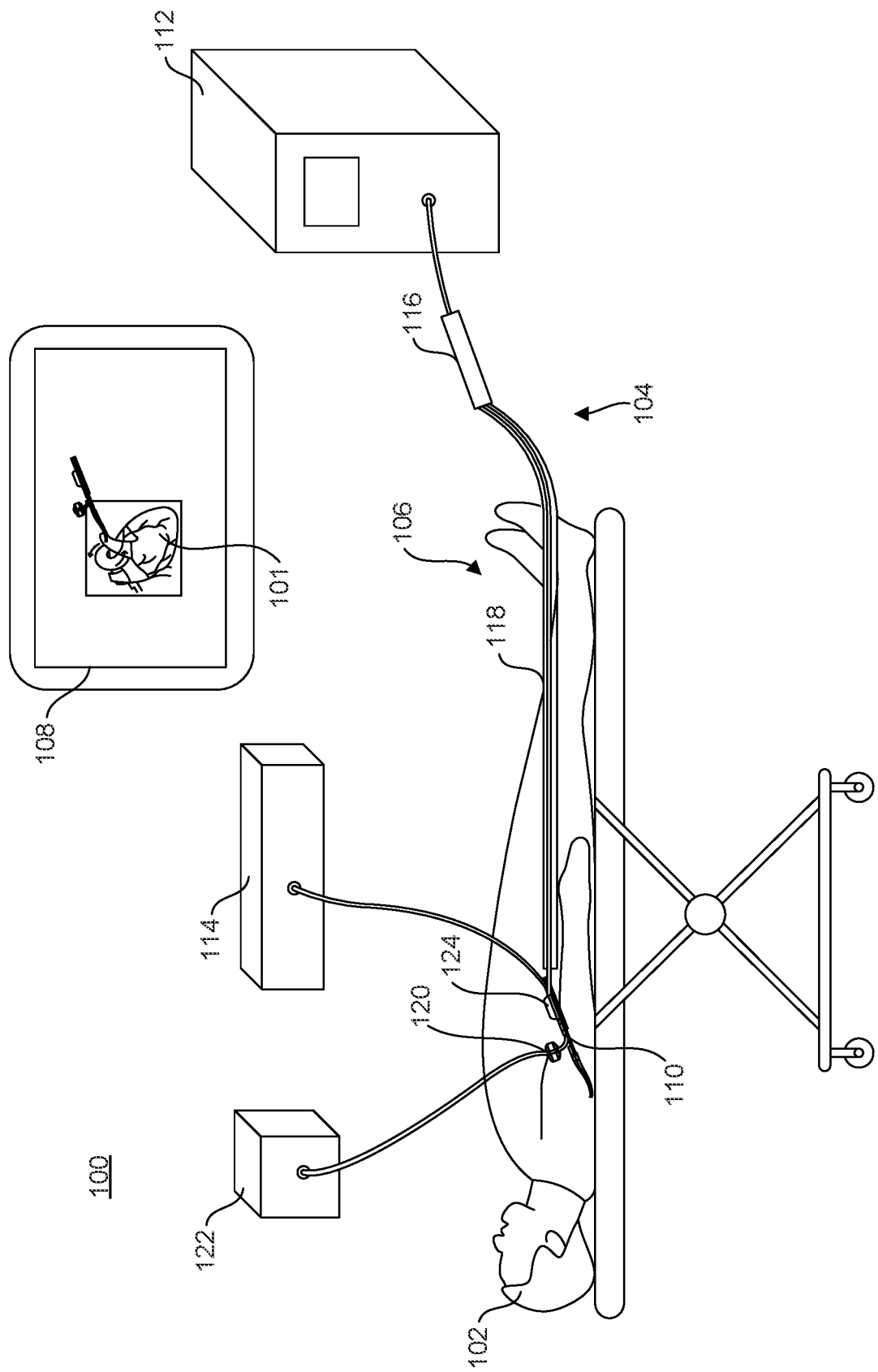
FIG. 1 is a diagram illustrating an exemplary clinical setting for treating a heart of the patient, using a shunting catheter system, in accordance with embodiments of the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, and/or dimensions are provided for selected elements. Those skilled in the art will recognize that many of the noted examples have a variety of suitable alternatives.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g., 1 to 5 includes 1, 1.5, 2, 2.75, 3, 3.80, 4, and 5) and any number within that range.

Although illustrative methods may be represented by one or more drawings (e.g., flow diagrams, communication flows, etc.), the drawings should not be interpreted as implying any requirement of, or particular order among or between, various steps disclosed herein. However, some embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information. In some embodiments, the term "receive" or "receiving" means obtaining from a data repository (e.g., database), from another system or service, from another software, or from another software component in a same software. In certain embodiments, the term "access" or "accessing" means retrieving data or information, and/or generating data or information.

There are various approaches for creating an interatrial shunt, which is a connection or gateway between the left and right atria of a patient's heart for blood to flow through. In some embodiments, examples of interatrial shunt devices (IASDs) include implants or shunting catheters. For example, devices reside in the interatrial septum, with risk for right-to-left shunting and systemic embolization. In some examples, preservation of the interatrial septum is important with an increasing number of left-sided transseptal transcatheter interventions. Ways to improve IASDs for safer and better procedures are needed. At least some embodiments of the present disclosure are directed to a shunting catheter for deployment through a patient's coronary sinus (CS) for creating a shunt between the CS and the patient's left atrium (LA). At least some embodiments of the present disclosure are directed to a shunting catheter for deployment through a patient's atrial septum (AS) for atrial septal shunting.

A patient's CS ostium may have a diameter of from about 10 mm to about 20 mm. As the CS is a relatively small vessel, at least some embodiments of the present disclosure are directed to features of a shunting catheter that helps protect a patient's vessels during deployment and/or elements for stabilizing the catheter during the procedure. In embodiments, the shunting catheter includes a catheter shaft, a shunting element, and an apposition element disposed proximate to the shunting element. In some embodiments, the catheter shaft is made of flexible materials that bends according to the anatomy of the CS to conform to the shape of the patient's CS. In yet some embodiments, the catheter shaft includes a stabilizing element such as distal tip that has a curve (e.g., a pre-existing curve) conforming to the shape of a patient's CS to help stabilize the catheter and minimize potential damage to a patient's tissue wall (e.g., the vessel wall of a patient's CS).

In some embodiments, the apposition element is protruded from the catheter shaft during deployment to help stabilize the catheter at a desired location for creating the shunt. In certain embodiments, the shunting element further includes an expandable element (e.g., a balloon) and a tube (e.g., a hypotube) to support the expandable element. The tube may have a plurality of cuts along the tube to help facilitate bending of the tube. In some embodiments, a shunt is formed in a patient's CS vessel by creating an opening between the patient's CS and LA. In certain embodiments, the shunting catheter is inserted through the patient's superior vena cava (SVC) via a transjugular approach. In certain embodiments, the shunting catheter is inserted through the patient's inferior vena cava (IVC) via a transfemoral approach.

FIG. 1 is a diagram illustrating an exemplary clinical setting 100 for treating a heart 101 of the patient 102, using a shunting catheter system 104, in accordance with embodiments of the present disclosure. The shunting catheter system 104 includes a shunting device 106. As will be appreciated by the skilled artisan, the clinical setting 100 may have other components and arrangements of components that are not shown in FIG. 1. In some embodiments, the shunting catheter system 104 includes or is coupled to an imaging system (e.g., an X-ray system) which may include one or more visualization elements and a display 108. In some embodiments, one or more visualization elements may be disposed on the shunting device 106. In certain embodiments, the imaging system can help guide a physician's operation of the shunting catheter 110 during procedure.

The shunting device 106 includes a shunting catheter 110, a controller 112, and an energy source 114 (e.g., a generator). The controller 112 is configured to control functional aspects of the shunting device 106. In embodiments, the controller 112 is configured to control the energy source 114 to deliver energy to the shunting catheter 110. The controller 112 may be connected to the one or more visualization elements to facilitate positioning of the shunting catheter 110 in a patient's heart during procedure. In some embodiments, the energy source 114 is connected to the controller 112. In yet some embodiments, the energy source 114 may be incorporated into the controller 112.

As will be appreciated by the skilled artisan, the depiction of the shunting catheter system 104 shown in FIG. 1 is intended to provide a general overview of the various components of the shunting catheter system 104 and is not in any way intended to imply that the disclosure is limited to any set of components or arrangement of the components. For example, the skilled artisan will readily recognize that additional hardware components, e.g., breakout boxes, workstations, and the like, can and likely will be included in the shunting catheter system 104.

According to some embodiments, the shunting device 106 includes a handle 116, a catheter shaft 118, a puncture element (e.g., a puncture needle) configured to puncture through a tissue wall, and a shunting element 120 configured to provide shunting at a target location. In certain embodiments, the shunting element 120 is inflatable and connected to an inflation source 122. In some instances, the shunting element 120 includes an expandable element (e.g., a balloon). In certain embodiments, the shunting element 120 is connected to the energy source 114 to provide shunting. For example, the shunting element 120 includes electrodes to receive electrical power from the energy source 114 to deliver energy (e.g., ablative energy, radiofrequency (RF) energy, phased energy, thermal energy, cryogenic energy, pulse ablative energy (e.g., pulsed field ablation (PFA)), microwave energy, laser energy, ultrasound energy, etc.) to the target location (e.g., a target tissue) at a cardiovascular system (e.g., a circulatory system) wall.

In certain embodiments, the handle 116 is configured to be operated by a user to position the puncture element and the shunting element 120 at the desired anatomical location. The catheter shaft 118 generally defines a longitudinal axis of the shunting catheter 110. In some embodiments, the shunting element 120 may include a balloon connected to a shunting element shaft positioned within the catheter shaft 118 at a first state (e.g., before a deployment and/or during a deployment to position the shunting element 120). In certain embodiments, the shunting element shaft having a pre-determined curve. In some examples, the shunting element shaft has a pre-determined curve for the shunting element to deploy. In certain embodiments, the shunting element shaft is extended from the catheter shaft 118 at a second state (e.g., a shunting state to use the shunting element).

According to certain embodiments, during deployment, the shunting device 106 including the catheter shaft 118 enters through a patient's CS ostium located in the patient's right atrium. The shunting device 106 may then be oriented through one or more mechanisms in the patient's CS, as will be discussed in more details below. In some embodiments, in order to conform to the shape of the patient's CS, the catheter shaft 118 is made of flexible materials that may bend according to the anatomy of the CS.

In certain embodiments, the shunting catheter 110 includes an apposition element 124 disposed proximate to the shunting element 120. In some embodiments, the apposition element is disposed within a shaft (e.g., an outer shaft) at the first state. In some embodiments, the apposition element 124 is protruded from the catheter shaft 118 at the first state and/or at the second state. In certain embodiments, the apposition element 124 can appose to a cardiovascular system wall (e.g., the front wall or back wall of the CS, a left atrium wall, a right atrium wall, etc.) at the second state, for example, to help position and/or stabilize the shunting element 120. In certain embodiments, the apposition element 124 includes a braid structure. In some embodiment, the apposition element 124 may include a nitinol braid that can be held within the catheter shaft 118. After deployment and stabilization of the catheter shaft 118, the shunting element 120 including a puncture element may then be deployed. In some embodiments, the shunting element is configured to deliver energy to target tissues for creating a shunt in the patient's CS.

According to some embodiments, various components (e.g., the controller 112) of the shunting catheter system 104 may be implemented on one or more computing devices. A computing device may include any type of computing device suitable for implementing embodiments of the disclosure. Examples of computing devices include specialized computing devices or general-purpose computing devices such as workstations, servers, laptops, portable devices, desktop, tablet computers, hand-held devices, general-purpose graphics processing units (GPGPUs), and the like, all of which are contemplated within the scope of FIG. 1 with reference to various components of the shunting catheter system 104.

In some embodiments, a computing device (e.g., the controller 112) includes a bus that, directly and/or indirectly, couples the following devices: a processor, a memory, an input/output (I/O) port, an I/O component, and a power supply. Any number of additional components, different components, and/or combinations of components may also be included in the computing device. The bus represents what may be one or more busses (such as, for example, an address bus, data bus, or combination thereof). Similarly, in some embodiments, the computing device may include a number of processors, a number of memory components, a number of I/O ports, a number of I/O components, and/or a number of power supplies. Additionally, any number of these components, or combinations thereof, may be distributed and/or duplicated across a number of computing devices. In some embodiments, various components or parts of components (e.g., controller 112, shunting catheter 110, etc.) can be integrated into a physical device.

In some embodiments, the shunting catheter system 104 includes one or more memories (not illustrated). The one or more memories includes computer-readable media in the form of volatile and/or nonvolatile memory, transitory and/or non-transitory storage media and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In some embodiments, the one or more memories store computer-executable instructions for causing a processor (e.g., the controller 90) to implement aspects of embodiments of system components discussed herein and/or to perform aspects of embodiments of methods and procedures discussed herein.

Computer-executable instructions may include, for example, computer code, machine-useable instructions, and the like such as, for example, program components capable of being executed by one or more processors associated with a computing device. Program components may be programmed using any number of different programming environments, including various languages, development kits, frameworks, and/or the like. Some or all of the functionality contemplated herein may also, or alternatively, be implemented in hardware and/or firmware.

In some embodiments, the memory may include a data repository that may be implemented using any one of the configurations described below. A data repository may include random access memories, flat files, XML files, and/or one or more database management systems (DBMS) executing on one or more database servers or a data center. A database management system may be a relational (RDBMS), hierarchical (HDBMS), multidimensional (MDBMS), object oriented (ODBMS or OODBMS) or object relational (ORDBMS) database management system, and the like. The data repository may be, for example, a single relational database. In some cases, the data repository may include a plurality of databases that can exchange and aggregate data by a data integration process or software application. In an exemplary embodiment, at least part of the data repository may be hosted in a cloud data center. In some cases, a data repository may be hosted on a single computer, a server, a storage device, a cloud server, or the like. In some other cases, a data repository may be hosted on a series of networked computers, servers, or devices. In some cases, a data repository may be hosted on tiers of data storage devices including local, regional, and central.

Various components of the shunting catheter system 104 can communicate via or be coupled to via a communication interface, for example, a wired or wireless interface. The communication interface includes, but is not limited to, any wired or wireless short-range and long-range communication interfaces. The wired interface can use cables, umbilicals, and the like. The short-range communication interfaces may be, for example, local area network (LAN), interfaces conforming to known communications standards, such as Bluetooth™ standard, IEEE 802 standards (e.g., IEEE 802.11), a ZigBee™ or similar specification, such as those based on the IEEE 802.15.4 standard, or other public or proprietary wireless protocol. The long-range communication interfaces may be, for example, wide area network (WAN), cellular network interfaces, satellite communication interfaces, etc. The communication interface may be either within a private computer network, such as intranet, or on a public computer network, such as the internet. Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

Figure 2:
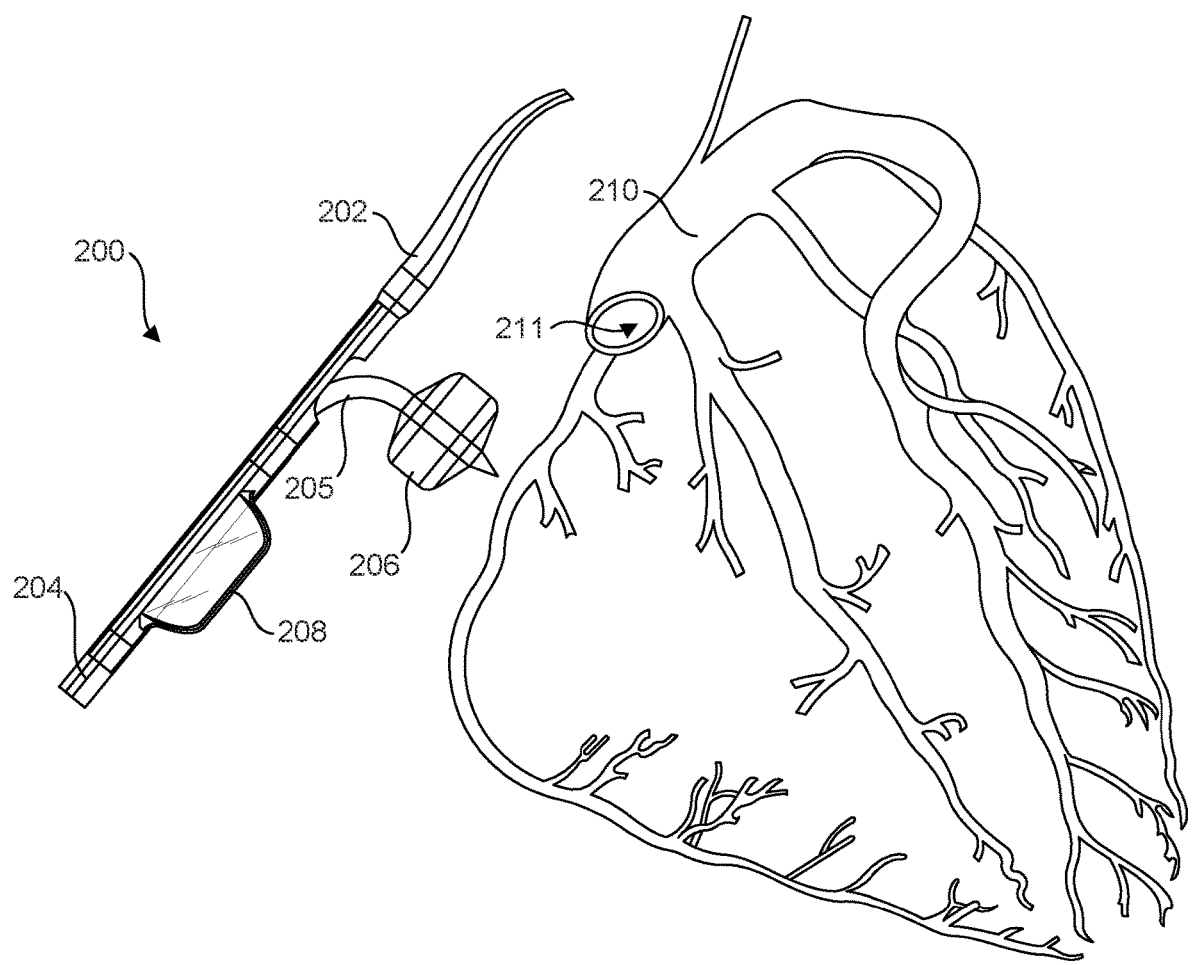
FIG. 2 is a schematic diagram illustrating an example of a shunting device to be deployed in a heart of a patient, in accordance with embodiments of the present disclosure.

FIG. 2 is a schematic diagram illustrating an example of a shunting device 200 to be deployed in a heart of a patient, in accordance with embodiments of the present disclosure. FIG. 2 is merely an example. One of the ordinary skilled in the art would recognize many variations, alternatives, and modifications. As shown, the shunting device 200 includes a shunting catheter 202 to be delivered through a patient's coronary sinus (CS) 210 via the CS ostium 211. In some embodiments, the shunting catheter 202 includes a catheter shaft 204, a shunting element 206, and an apposition element 208. In certain embodiments, the catheter shaft 204 has a curve at its distal end 205. In some embodiments, as illustrated, the shunting element 206 is extended from the catheter shaft 204 at a second state (e.g., a state to provide shunting). In certain examples, the shunting element 206 forms an angle greater than 10 degrees From the distal end 205 of the catheter shaft 204. In some examples, the shunting element 206 forms an angle greater than 30 degrees From the distal end 205 of the catheter shaft 204. In some embodiments, the shunting element 206 forms an angle proximate to 90 degrees From the catheter shaft 204. In some embodiments, the shunting element 206 forms an angle in the range of 10 degrees to 120 degrees From the catheter shaft 204.

In some embodiments, the catheter shaft 204 is made of flexible material that may curve with the anatomy of the patient's CS 210. In certain embodiments, for example, the catheter shaft 204 may include polyether block amide, nylon, silicone, or a combination thereof. In some instances, the catheter shaft 204 may be a multi-layered and multi-material component. In some examples, the catheter shaft 204 is reinforced with a braid and/or can have an etched or casted liner. The braid for reinforcing the catheter shaft 204 may be made of nitinol. The liner may be made from polyetheretherketone (PEEK), polytetrafluoroethylene (PTFE), copolymers of polyamide and polyether, or a combination thereof. In some embodiments, the catheter shaft 204 is coated for lubricity with a hydrophilic coating, or other types of coating suitable for coating a catheter shaft as known by a skilled person in the art.

In some embodiments, the shunting catheter 202 has a diameter of from about 2 mm to about 5 mm. In certain embodiments, the shunting catheter 202 has a diameter from about 2.5 mm to about 4.5 mm. In some embodiments, the shunting catheter has a diameter from about 3 mm to about 4 mm. In certain embodiments, the shunting catheter 202 may have a diameter allowing it to pass through vessels and parts of the cardiovascular system to reach a target location.

Figure 3:
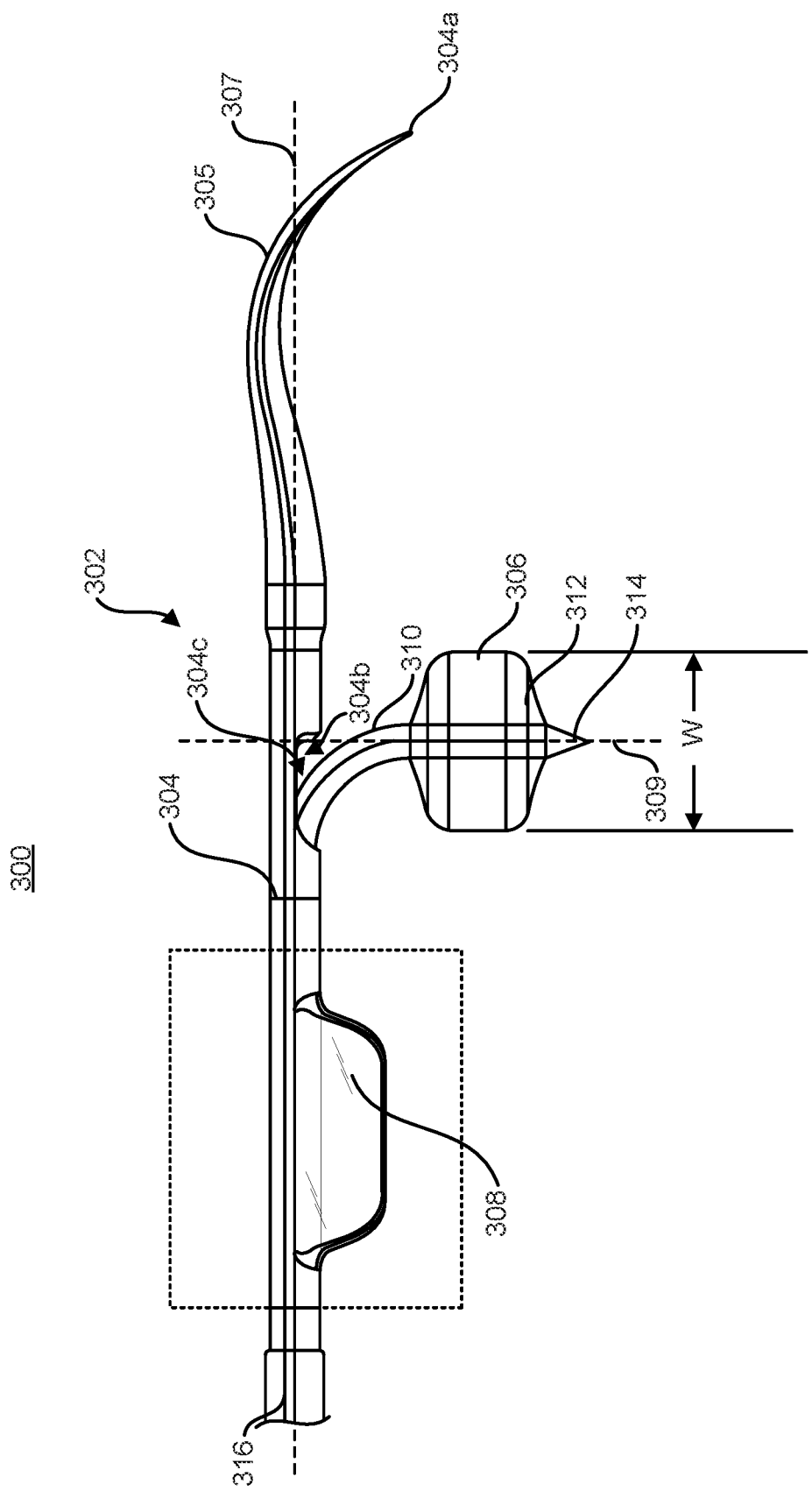
FIG. 3 is a schematic diagram of a side view of an example of a shunting device and a perspective view of an apposition element of the shunting device, in accordance with embodiments of the present disclosure.

FIG. 3 is a schematic diagram of a side view of an example of a shunting device 300 and a perspective view of an apposition element 308 of the shunting device 300, in accordance with embodiments of the present disclosure. FIG. 3 is merely an example. One of the ordinary skilled in the art would recognize many variations, alternatives, and modifications. As shown, the shunting device 300 includes a shunting catheter 302 to be delivered through a patient's coronary sinus (CS). The shunting catheter 302 includes a catheter shaft 304, a shunting element 306, and an apposition element 308.

According to certain embodiments, the catheter shaft 304 has a distal end 304a, a proximal end (not shown), and a shaft lumen 304b. In some embodiments, the catheter shaft 304 is made of flexible material that may curve with the anatomy of the patient's CS. In certain embodiments, the catheter shaft 304 may include polyether block amide, nylon, silicone, and/or a combination thereof. In some instances, the catheter shaft 304 may be a multi-layered and multi-material component. In some examples, the catheter shaft 304 is reinforced with a braid and can have an etched or casted liner. The braid for reinforcing the catheter shaft 304 may be made of nitinol. The liner may be made from polyetheretherketone (PEEK), polytetrafluoroethylene (PTFE), copolymers of polyamide and polyether, or a combination thereof. In certain embodiments, the catheter shaft 304 may be injection molded or extruded. In some embodiments, the catheter shaft 304 is coated for lubricity with a hydrophilic coating, or other types of coating suitable for coating a catheter shaft as known by a skilled person in the art. In some instances, the catheter shaft 304 may have multiple lumens.

According to some embodiments, the catheter shaft 304 may include a stabilizing element such as distal tip 305 at the distal end 304a that has a curve (e.g., a pre-existing curve), for example, a curve conforming to the anatomy of a patient's CS. In some instances, the distal tip 305 may be made of a different material than other parts of the catheter shaft 304. In some instances, for example, the distal tip 305 may be made of a material more flexible than the material of other parts of the catheter shaft 304. The distal tip 305 may be injection molded or machined to have a unique geometry (e.g., a curve) for better stabilizing the catheter shaft 304 during deployment.

According to some embodiments, the distal tip 305 may have a length of from about 5 mm to about 85 mm. In certain embodiments, the catheter shaft 304 includes a shaft opening 304c. In some embodiments, a portion of the catheter shaft from the shaft opening 304c and the distal end 304a has a curve. In some embodiments, the catheter shaft 304 defines a first axis 307, and the shunting element 306 defines a second axis 309 at the second state after deployment. In certain embodiments, the second axis 309 and the first axis 307 form an angle greater than zero degree.

According to certain embodiments, the shunting element 306 is disposed in the shaft lumen 304b at a first state. In some embodiments, the shunting element 306 includes an expandable element 312, also referred to as a balloon or a balloon element, connected to a shunting element shaft 310 on one end, and a puncture element 314 (e.g., a needle) on the other end. In certain embodiments, the expandable element 312 is an elongated element. The shunting element 306 may be connected to the shunting element shaft 310 positioned within the shaft lumen 304b of the catheter shaft 304 at a first state (e.g., during deployment, during deployment to position the shunting element 306). In certain embodiments, the shunting element shaft 310 has a pre-determined curve. In some examples, the shunting element shaft 310 has a pre-determined curve for the shunting element 306 to deploy. In certain embodiments, the shunting element shaft is extended from the shaft lumen 304b of the catheter shaft 304 at a second state (e.g., a shunting state to use the shunting element). In some examples, the expandable element 312 may be a balloon configured to deliver energy (e.g., ablative energy, radiofrequency (RF) energy, phased RF energy, thermal energy, cryogenic energy, pulse ablative energy (e.g., pulsed field ablation (PFA)), microwave energy, laser energy, ultrasound energy, etc.) to target tissue, and is expanded when the shunting element 306 is at a second state.

According to certain embodiments, the width of the expandable element 312 (w) can range from about 3 mm to about 15 mm. In some embodiments, the width of the expandable element 312 (w) can range from about 3.5 mm to about 12 mm. In certain embodiments, the width of the expandable element 312 (w) can range from about 4 mm to about 10 mm. In some embodiments, the width of the expandable element 312 (w) can range from about 4.5 mm to about 8 mm.

According to some embodiments, the shunting catheter 302 further includes an outer shaft 316 disposed outside of at least a part of the catheter shaft 304 during deployment. In some embodiments, the outer shaft 316 is made of flexible material that may curve with the anatomy of the patient's CS. In certain embodiments, for example, the outer shaft 316 may include polyether block amide, nylon, silicone, or a combination thereof. In some instances, the outer shaft 316 may be a multi-layered and multi-material component. In some examples, the outer shaft 316 is reinforced with a braid and can have an etched or casted liner. The braid for reinforcing the catheter shaft 304 may be made of nitinol. The liner may be made from polyetheretherketone (PEEK), polytetrafluoroethylene (PTFE), copolymers of polyamide and polyether, or a combination thereof. In certain embodiments, the outer shaft 316 may be injection molded or extruded. In some embodiments, the catheter shaft 304 is coated for lubricity with a hydrophilic coating, or other types of coating suitable for coating a catheter shaft as known by a skilled person in the art.

According to certain embodiments, the apposition element 308 is disposed within the outer shaft 316 at a first state (e.g., during deployment). In embodiments, the apposition element 308 protrudes from the catheter shaft 304 during deployment. The apposition element 308 is flexible and compressed to fit within the outer shaft 316, and configured to decompress and protrude from the catheter shaft 304 during deployment. In some embodiments, the apposition element 308 is disposed proximate to the shunting element 306 and/or the one or more shaft opening 304c. In some instances, the apposition element 308 is a braided structure including one or more nickel titanium wires. In yet some instances, the apposition element 308 is made of a flexible material having a portion protruding from the catheter shaft 304. In some examples, the flexible material may be a foam. In some instances, the flexible material may be a balloon filled with a contrast solution that shows up under fluoroscopy. In yet some instances, the flexible material may be a polymer with a radiopaque marker added for visualization. The radiopaque marker may include tantalum, gold, or any radiopaque maker known by a skilled person in the art.

In certain embodiments, the apposition element 308 is configured to appose at least one wall in a patient's CS or LA such that the shunting catheter 302 is stabilized in one position once deployed. According to some embodiments, the apposition element 308 has several benefits, one of which is the stabilization of catheter 302 after deployment. Any movement or lack thereof the protruding element (e.g., braided element 318) provides an estimated distance of how far the catheter 302 is away from a tissue wall (e.g., the vessel wall of a patient's CS). In addition, in instances where the apposition element 308 includes a braided element 318, even when the element 318 is apposing a tissue wall (e.g., the vessel wall of a patient's CS), the openings between the braids still allow blood flow through the apposition element 308, thus reducing the risk of thrombus formation caused by any occlusion in the vessel.

Figure 4:
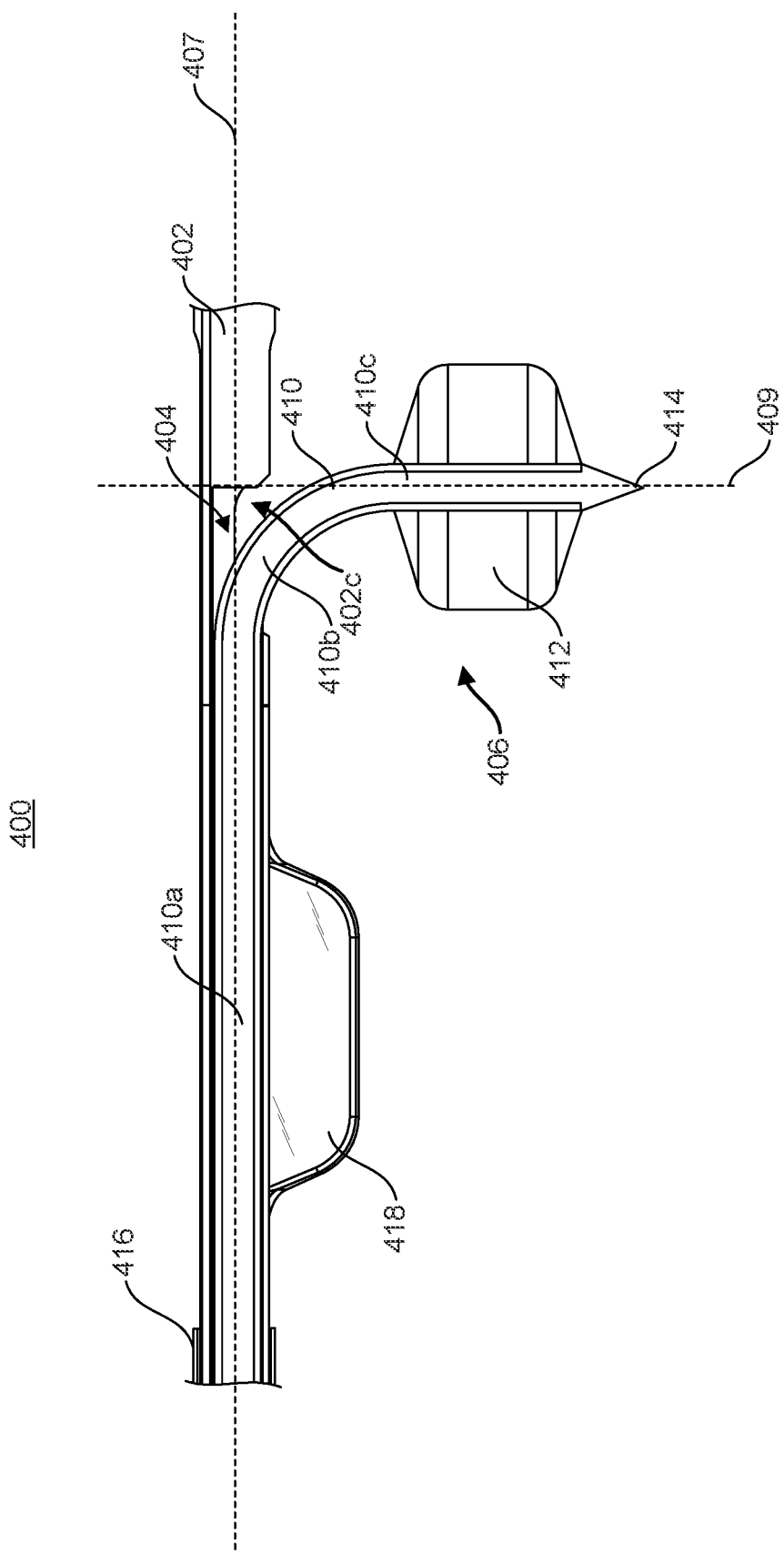
FIG. 4 is schematic diagrams of a cross-sectional view of an example of a shunting catheter, in accordance with embodiments of the present disclosure.

FIG. 4 is a schematic diagram of a cross-sectional view of an example of a shunting catheter 400, in accordance with embodiments of the present disclosure. As shown, the shunting catheter 400 includes a catheter shaft 402 having a shaft lumen 404, and a shunting element 406 disposed within the shaft lumen 404 at a first state (e.g., during deployment).

In some embodiments, the shunting element 406 is extended from the catheter shaft 402 at a second state. The shunting element 406 may include an expandable element 412 (e.g., a balloon) connected to a shunting element shaft 410 on one end, and a puncture element 414 (e.g., a needle) on the other end. In some examples, the expandable element 412 may be a balloon configured to deliver energy (e.g., ablative energy, radiofrequency (RF) energy, phased RF energy, thermal energy, cryogenic energy, pulse ablative energy (e.g., pulsed field ablation (PFA)), microwave energy, laser energy, ultrasound energy, etc.) to target tissue. In some embodiments, the shunting element 406 is positioned within the catheter shaft 402 at a first state (e.g., during a deployment to position the shunting element 406). In certain embodiments, the shunting element shaft 410 has a pre-determined curve. In some examples, the shunting element shaft 410 has a pre-determined curve for the shunting element 406 to deploy. In certain embodiments, the shunting element shaft 410 is extended from the catheter shaft 402 at a second state (e.g., a shunting state, a shunting state to use a shunting element).

According to some embodiments, the catheter shaft 402 includes a shaft opening 402*c*. In some embodiments, the catheter shaft 402 defines a first axis 407, and the shunting element 406 defines a second axis 409. In certain embodiments, the expandable element 412 is an elongated element, which has a length along the second axis 409 that is larger than a width perpendicular to the second axis 409. In certain embodiments, the second axis 409 and the first axis 407 form an angle greater than zero degree. In certain examples, the second axis 409 and the first axis 407 form an angle greater than 10 degrees. In some embodiments, the second axis 409 and the first axis 407 form an angle proximate to 90 degrees. In some embodiments, the second axis 409 and the first axis 407 form an angle in the range of 30 degrees to 120 degrees. In some instances, the catheter shaft 402 includes a pre-curve formed from a semi-rigid or rigid material connected to the puncture element 414. The semi-rigid or rigid material may include nitinol or stainless steel (SS) with a curve built in before deployment.

In some embodiments, the shunting element shaft 410 includes a curved portion 410*b* that forms an arc connecting a first straight portion of shunting element shaft 410*a* disposed inside the shaft lumen 404 and a second straight portion 410*c* of the shunting element shaft 410 extended outward from the shaft lumen 404. In embodiments, for example as shown, the curved portion 410*b* of the shunting element shaft 410 is adjacent the shaft opening 402*c*. In certain embodiments, the expandable element 412 is located at the second straight portion 410*c* and outside of the curved portion 410*b* of the shunting element shaft 410. In some embodiments, the expandable element 412 is an elongated element.

According to certain embodiments, the shunting catheter 400 may further include an outer shaft 416 disposed outside of the catheter shaft 402 and enclosing the catheter shaft 402, the apposition element 418 in a compressed state before shunting, and the shunting element 406. The outer shaft 416 may have a diameter of from about 8 to about 18 french, or from about 8.5 to about 16 french, or from about 9 to about 14 french, or from about 9.5 to about 12 french, or may have a diameter encompassed within these ranges. In some embodiments, for example during deployment, the outer shaft 416 is pulled back to deploy and/or position the catheter shaft 402 including the apposition element 418 and the shunting element 406.

In certain embodiments, the shunting catheter 400 includes multiple compartments (e.g., lumens) for various elements to provide more targeted control during deployment. For example, the shunting catheter 400 may include an additional lumen in between the catheter shaft 402 and the shunting element shaft 410 for more precise control during deployment of the shunting element 406. Similarly, for example, the shunting catheter 400 may include an additional lumen in between outer shaft 416 and the catheter shaft 402 for more precise control during deployment of the apposition element 418. In some embodiments, the shunting catheter 400 may include lumens for containing functional components such as a guidewire or pull wire assembly, as will be discussed further below. In yet some embodiments, the shunting catheter 400 may include additional lumens for holding shunted tissue from a tissue wall.

Figure 5A:
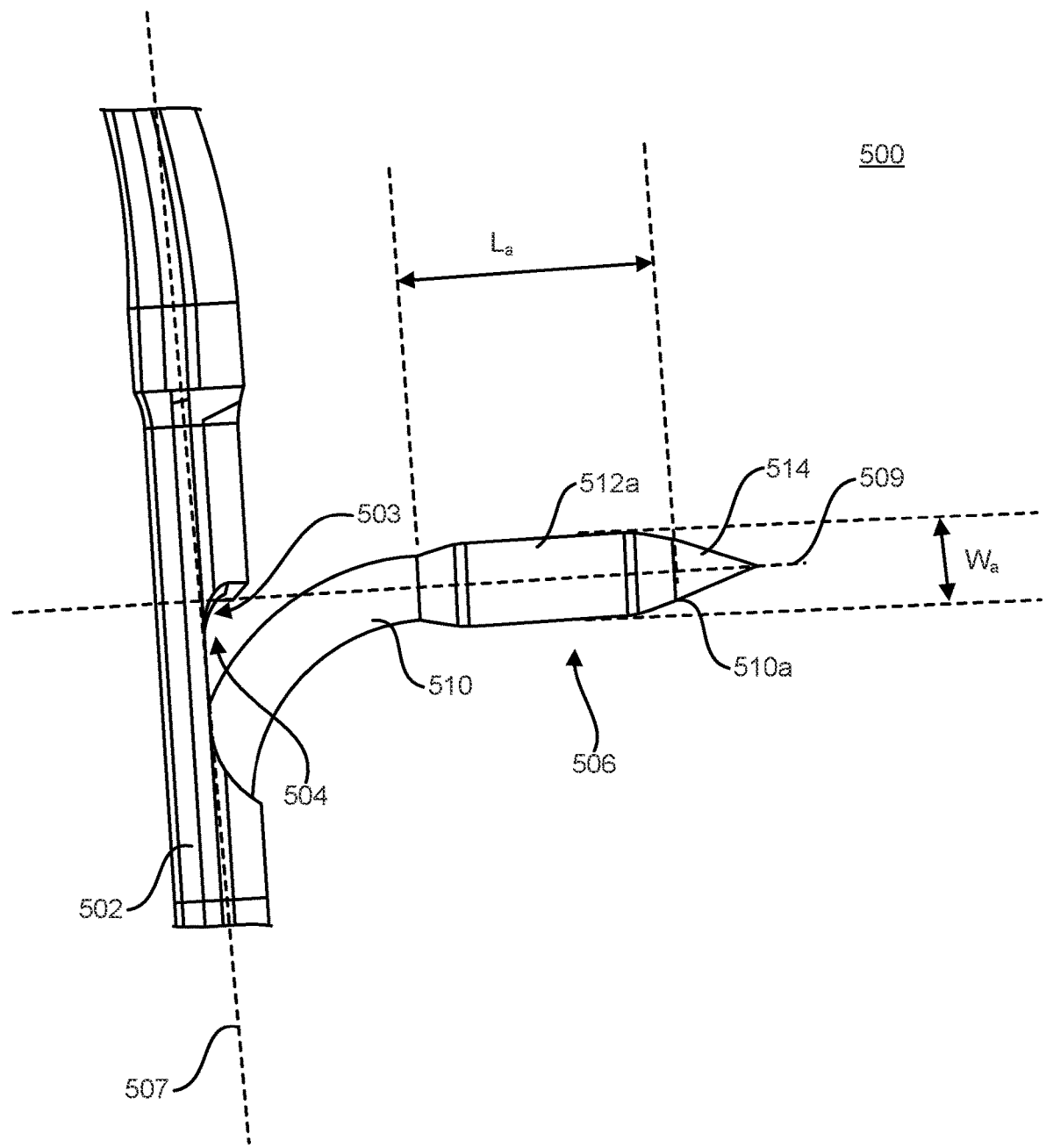
FIGS. 5A-5C are schematic diagrams of an example of a shunting catheter, in accordance with embodiments of the present disclosure.
Figure 5B:
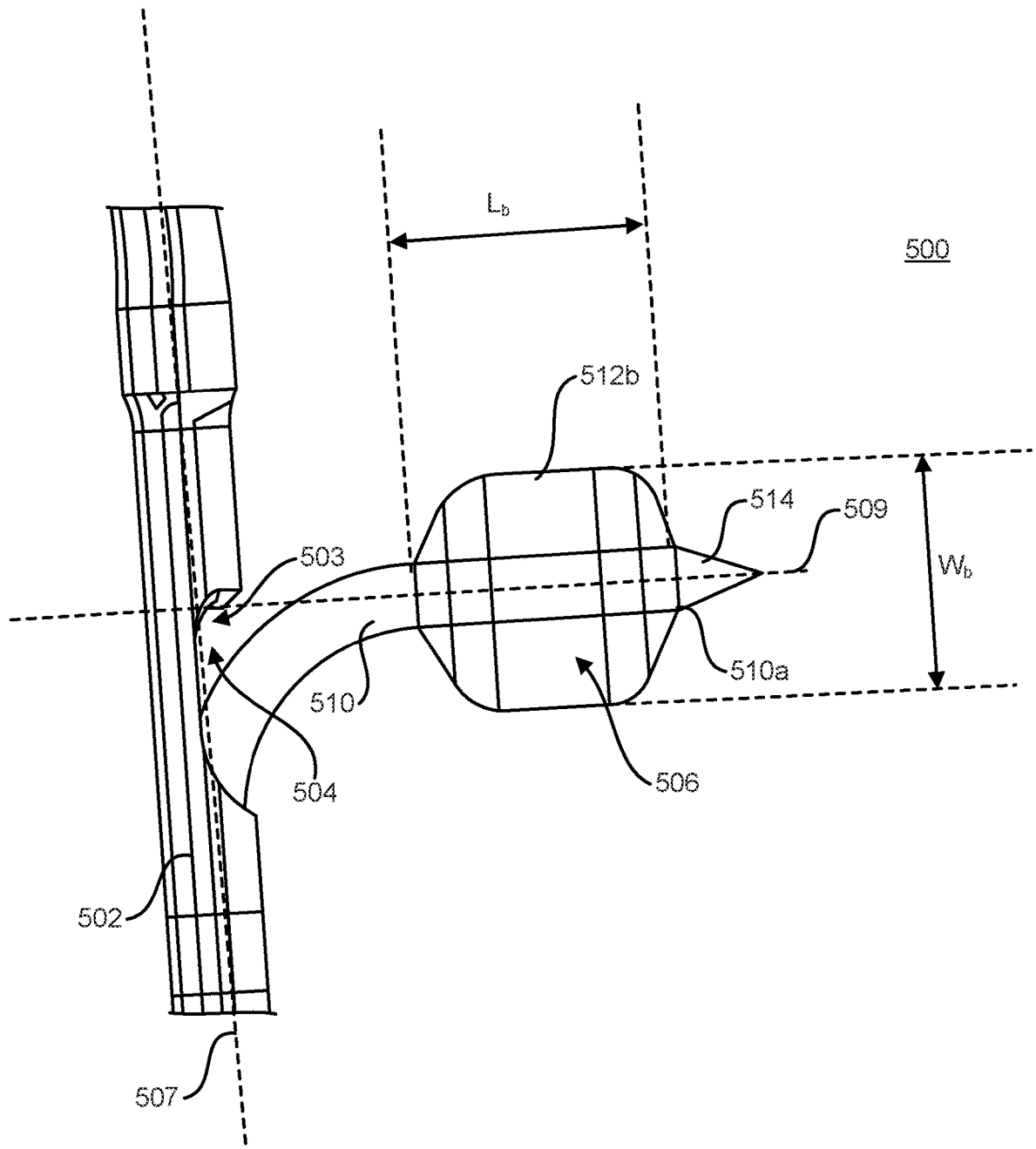
Figure 5C:
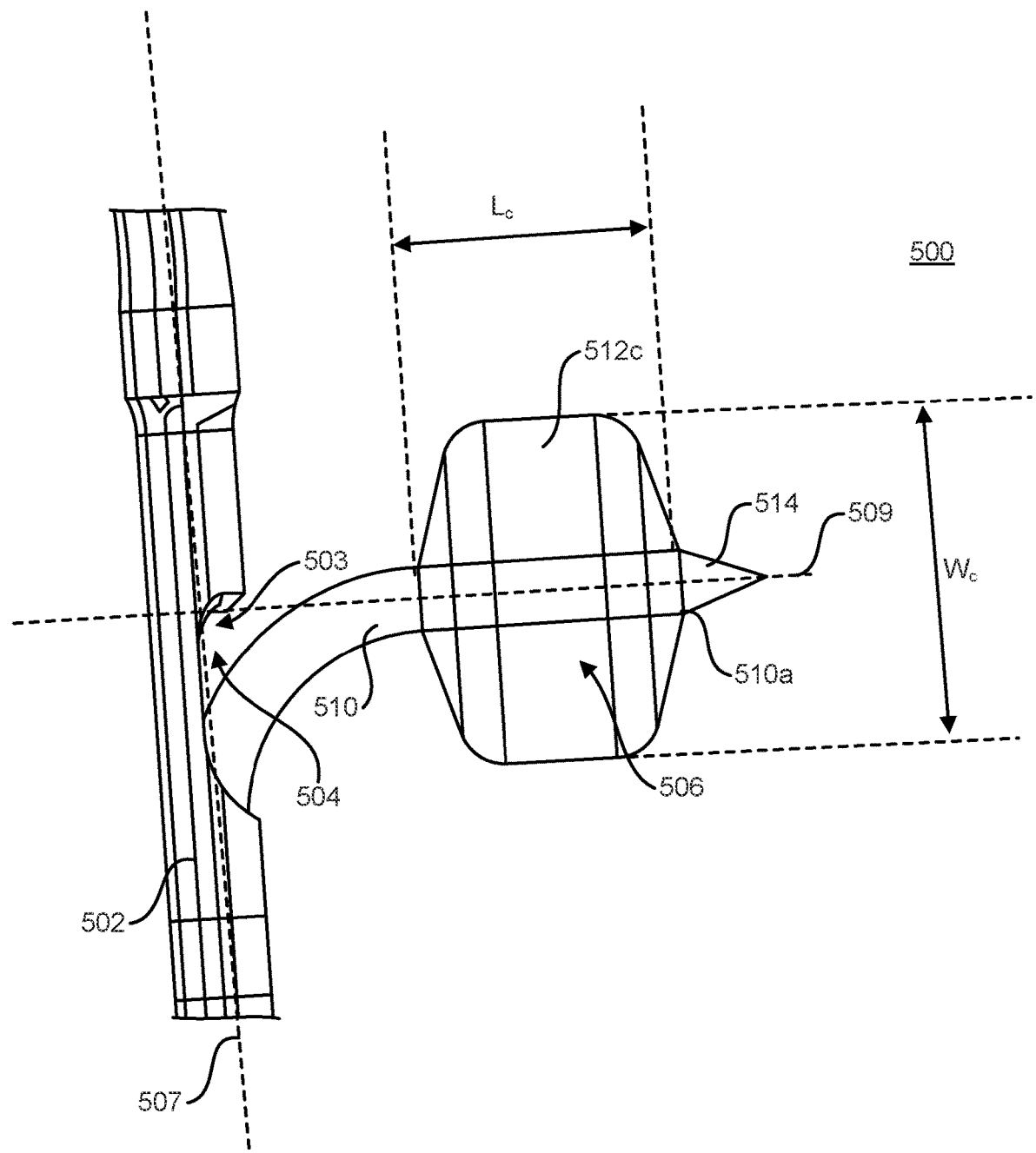

FIGS. 5A-5C are schematic diagrams of an example of a shunting catheter 500, in accordance with embodiments of the present disclosure. As shown, the shunting catheter 500 includes a catheter shaft 502 having a shaft opening 503, a shaft lumen 504, and a shunting element 506 disposed within the shaft lumen 504 at a first state.

In some embodiments, for example as shown in FIGS. 5A-5C, the shunting element 506 is extended from the catheter shaft 502 at a second state. In embodiments, the shunting element 506 includes a balloon element 512*a-c* connected to a balloon shaft 510. In certain embodiments, the balloon shaft is disposed in the shaft lumen 504 at a first state and extended from the catheter shaft 502 at a second state. In certain embodiments, the balloon shaft 510 has a pre-determined curve for the shunting element 506 to deploy. The balloon shaft 510 may be further connected to a puncture element 514 (e.g., a needle). In some examples, the balloon element 512*a-c* is configured to deliver energy (e.g., ablative energy, radiofrequency (RF) energy, phased RF energy, thermal energy, cryogenic energy, pulse ablative energy (e.g., pulsed field ablation (PFA)), microwave energy, laser energy, ultrasound energy, etc.) to treat surrounding tissues.

In certain embodiments, the balloon element 512*a-c* is made of material including nylon, copolymers of polyamide and polyether, polyethylene terephthalate (PET), polyurethane (PU), silicone, thermoplastic polyurethanes, polyamides, or a combination thereof. In some instances, the balloon element 512*a-c* is multilayered. In certain instances, the balloon element 512*a-c* is disposed on the balloon shaft 510 and expandable at the second state of the shunting element 506 during deployment. In some embodiments, the balloon element 512*a-c* includes at least one electrode of one or more electrodes disposed on the balloon element 512*a-c*.

According to some embodiments, the balloon element 512*a-c* is disposed at the distal end 510*a* of the balloon shaft 510, and includes a plurality of states during deployment. In certain embodiments, the balloon element 512*a-c* includes at least two states (e.g., a deployment state, an operation state, etc.). In some embodiments, the balloon element 512*a-c* includes three or more states. In some embodiments, for example as shown in FIG. 5A, the balloon element 512*a* is in a compressed state. In some instances, the balloon element 512*a* is crimped when in a compressed state. In certain instances, the balloon element 512*a* includes multiple layers when in a compressed state. In some examples, the balloon element 512*a* may be made of a relatively thicker and/or rigid material, and is folded into pleats when in a compressed state. In certain examples, the balloon element 512*a* may be made of a relatively thinner and/or flexible material, and includes one layer when in a compressed state. In some embodiments, for example as shown in FIG. 5B, the balloon element 512b is expanded to a first inflated state (e.g., a semi-inflated state). In some embodiments, for example as shown in FIG. 5C, the balloon element 512c is expanded to a second inflated state (e.g., a fully inflated state).

According to certain embodiments, the catheter shaft 502 defines a first axis 507, and the balloon shaft 510 defines a second axis 509. In certain embodiments, the second axis 509 and the first axis 507 form an angle greater than zero degree. In certain examples, the second axis 509 and the first axis 507 form an angle greater than 20 degrees. In certain examples, the second axis 509 and the first axis 507 form an angle greater than 10 degrees. In some embodiments, the second axis 509 and the first axis 507 form an angle proximate to 45 degrees. In some embodiments, the second axis 509 and the first axis 507 form an angle in the range of 30 degrees to 120 degrees. In certain examples, the second axis 509 and the first axis 507 form an angle proximate to 90 degrees.

According to some embodiments, the balloon element 512a, when in a compressed state, has a balloon length ($L_a$) along the second axis 509 and a balloon width ($W_a$) perpendicular to the second axis 509. The balloon length $L_a$ may be from about 4 mm to about 20 mm. The balloon width $W_a$ may be from about 1 mm to about 5 mm. In some instances, the balloon element 512a is in a compressed state at a first state of the shunting element 506 (e.g., during deployment). In some instances, the balloon element 512a is in a compressed state when the puncture element 514 is used to puncture through a tissue wall. In certain instances, the balloon element 512a is in a compressed state such that the width of the balloon element 512a is smaller than the diameter of a vessel (e.g., coronary sinus) of a patient.

According to certain embodiments, the balloon element 512b, when in a first inflated state, has a balloon length ($L_b$) along the second axis 509 and a balloon width ($W_b$) perpendicular to the second axis 509. In some embodiments, the length of the balloon 512b ($L_b$) is greater than the width of the balloon 512b ($W_b$) when the balloon element is in an inflated state. The length of the balloon 512b ($L_b$) may be the same as or similar to the length of the balloon 512a ($L_a$). In certain embodiments, the width of the balloon 512b ($W_b$) when in a semi-inflated state can range from about 1 mm to about 12 mm, or from about 1 mm to about 10 mm, or from about 2 mm to about 10 mm, or from about 2 mm to about 9 mm, or from about 2 mm to about 8 mm, or from about 2 mm to about 7 mm, or from about 2 mm to about 6 mm, or may be in a range encompassed within these ranges. In certain instances, the balloon element 512b is in a first inflated state and configured to treat surrounding tissue by delivering energy or chemical to the surrounding tissue.

According to some embodiments, the balloon element 512c, when in a second inflated state, has a balloon has a balloon length ($L_c$) along the second axis 509 and a balloon width ($W_c$) perpendicular to the second axis 509. In some embodiments, the length of the balloon 512c ($L_c$) is greater than the width of the balloon 512c ($W_c$) when the balloon element is in a second inflated state. The length of the balloon 512c ($L_c$) may be the same as or similar to the length of the balloon 512b ($L_b$). In some instances, for example as shown in FIG. 5C, the balloon element 512c is expanded to a second inflated state (e.g., a fully inflated state). In some embodiments, the balloon element 512c is an elongated element. In certain embodiments, the width of the balloon 512c ($W_c$) can range from about 3 mm to about 15 mm, or from about 3 mm to about 12 mm, or from about 3.5 mm to about 12 mm, or from about 4 mm to about 10 mm, or from about 4.5 mm to about 10 mm, or from about 5 mm to about 10 mm, or from about 5 mm to about 8 mm, or may be in a range encompassed within these ranges. In certain instances, the balloon element 512c is in a second inflated state (e.g., fully inflated state) and configured to treat surrounding tissue by delivering energy or chemical to the surrounding tissue.

In some embodiments, the balloon element 512b-c is expanded to an inflated state at a second state of the shunting element 506 (e.g., during shunting). In some instances, the balloon element 512a is expanded to an inflated state from a compressed state after the puncture element 514 punctures through a tissue wall.

In some instances, after the balloon element 512a is expanded into balloon element 512b or 512c, energy (e.g., ablative energy, radiofrequency (RF) energy, phased RF energy, thermal energy, cryogenic energy, pulse ablative energy (e.g., pulsed field ablation (PFA)), microwave energy, laser energy, ultrasound energy, etc.) may be delivered to one or more electrodes disposed on the balloon element 512b or 512c to ablate tissue surrounding the balloon element 512b or 512c.

Figure 6A:
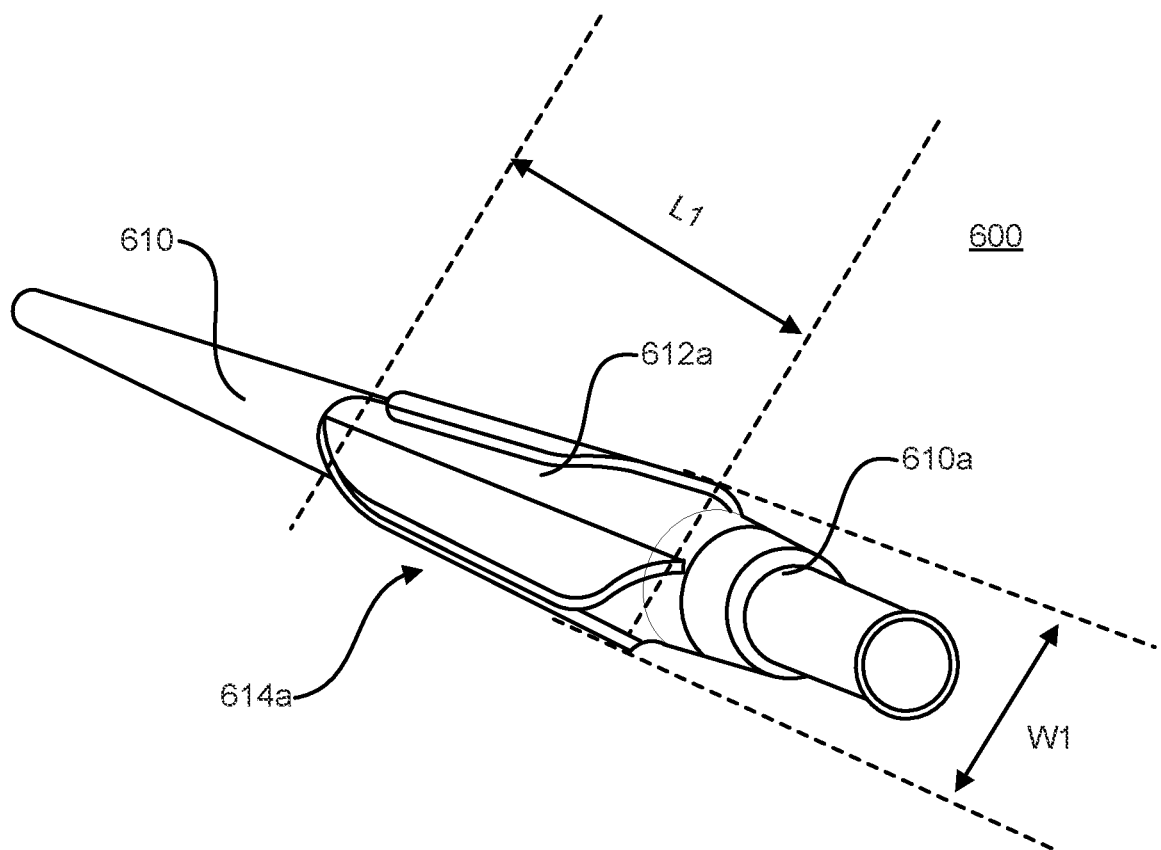
FIGS. 6A-6C are schematic diagrams of a perspective view of an example of a shunting element, in accordance with embodiments of the present disclosure.
Figure 6B:
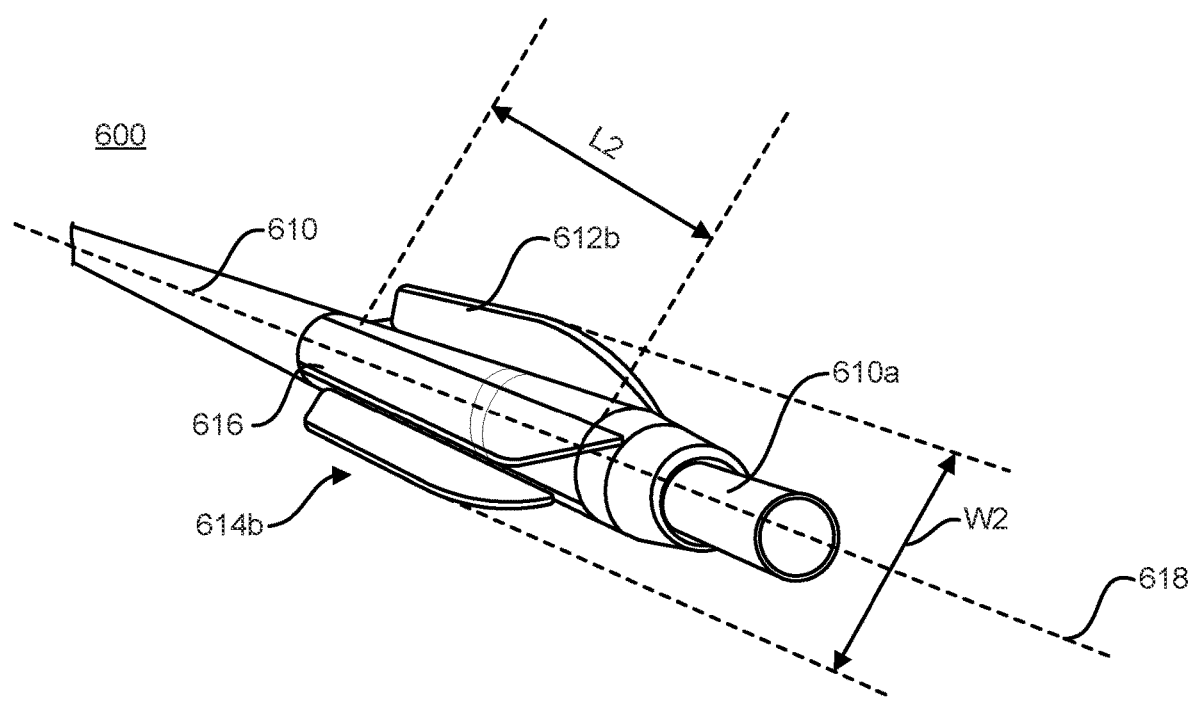
Figure 6C:
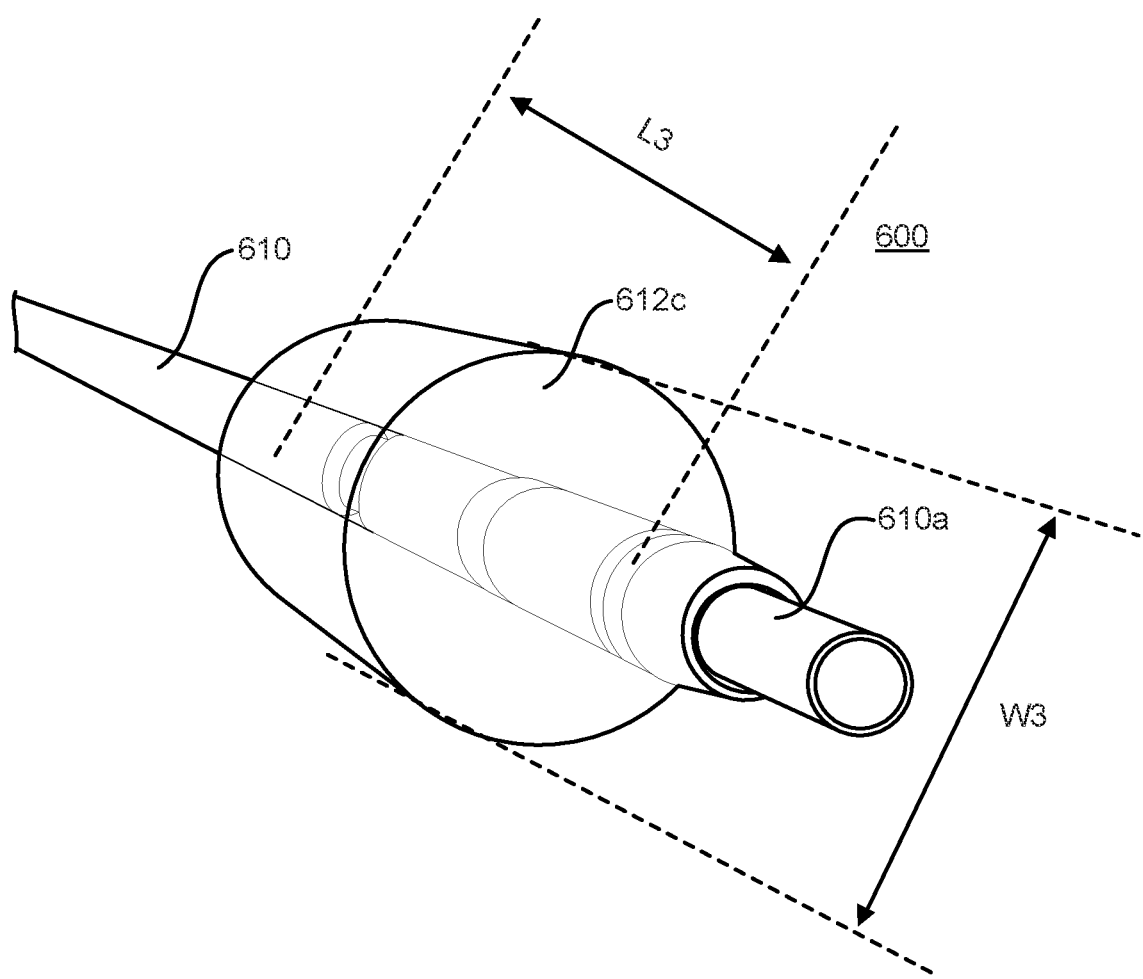

FIGS. 6A-6C are schematic diagrams of a perspective view of an example of a shunting element 600, in accordance with embodiments of the present disclosure. As shown, the shunting element 600 includes a balloon element 612a-c disposed on the distal end 610a of a balloon shaft 610. Each of the balloon elements 612a, 612b, and 612c has a length along the length of the balloon shaft 610 (L1, L2, and L3), and a width perpendicular to the length of the balloon shaft 610 (W1, W2, and W3). In embodiments, the balloon lengths L1, L2, and L3 are the same or similar to one another. In some embodiments, the balloon widths W1, W2, and W3 are different from one another.

According to certain embodiments, the balloon element 612a-c includes a membrane made of material including nylon, copolymers of polyamide and polyether, polyethylene terephthalate (PET), polyurethane (PU), silicone, thermoplastic polyurethanes, polyamides, or a combination thereof.

According to some embodiments, the balloon element 612a-c includes a plurality of states. In certain embodiments, the balloon element 612a-c includes three or more states. In some embodiments, for example as shown in FIG. 6A, the balloon element 612a is crimped and in a compressed state. In some embodiments, for example as shown in FIG. 6B, the balloon element 612b is expanded to a first inflated state (e.g., a semi-inflated state). In yet some embodiments, for example as shown in FIG. 6C, the balloon element 612c is expanded to a second inflated state (e.g., a fully inflated state).

In certain embodiments, the balloon element 612a has a length (L1) from about 4 mm to about 20 mm, and a width (W1) from about 1 mm to about 5 mm. In some instances, for example as shown in FIG. 6A, the balloon element 612a is in a compressed state having a pleated configuration, where the balloon element 612a is crimped into one or more flat pieces (e.g., one or more pleats 614a) that are folded over each other. In some instances, each pleat of the one or more pleats 614a may be of the same size and thickness.

In some embodiments, the balloon element 612b has a length (L2) from about 4 mm to about 20 mm, and a width (W2) from about 1 mm to about 5 mm. The length of the balloon 612b (L2) may be the same as or similar to the length of the balloon 612a (L1). In some instances, for example as shown in FIG. 6B, the balloon element 612b is expanded to a first inflated state (e.g., a semi-inflated state). In certain instances, the length of the balloon 612b (L2) is greater than the width of the balloon 612b (W2) when the balloon element is in a first inflated state. Each of the one or more pleats 614b of the balloon element 612b expands in thickness, and the outer edge of each of the pleats 614b, for example the outer edge 616 may have an average distance of from about 1 mm to about 5 mm to the axis 618 as defined by the balloon shaft 610. In certain instances, the balloon element 612b is in a first inflated state and configured to treat surrounding tissue by delivering energy or chemical to the surrounding tissue.

In certain embodiments, the balloon element 612c has a length (L3) from about 4 mm to about 20 mm. The length of the balloon element 612c (L3) may be the same as or similar to the length of the balloon element 612a (L1) and balloon element 612b (L2). In some instances, for example as shown in FIG. 6C, the balloon element 612c is expanded to a second inflated state (e.g., a fully inflated state). In some embodiments, the balloon element 612c is an elongated element. In certain instances, the length of the balloon 612c (L3) is greater than the width of the balloon 612c (W3) when the balloon element is in a second inflated state.

As shown, the balloon element 612c is fully expanded, and no longer has a pleated configuration. In some instances, the width of the balloon 512c (W3) can range from about 3 mm to about 15 mm, or from about 3 mm to about 12 mm, or from about 3.5 mm to about 12 mm, or from about 4 mm to about 10 mm, or from about 4.5 mm to about 10 mm, or from about 5 mm to about 10 mm, or from about 5 mm to about 8 mm, or may be in a range encompassed within these ranges. In certain instances, the balloon element 612c is in a second inflated state and configured to treat surrounding tissue by delivering energy or chemical to the surrounding tissue.

Figure 7:
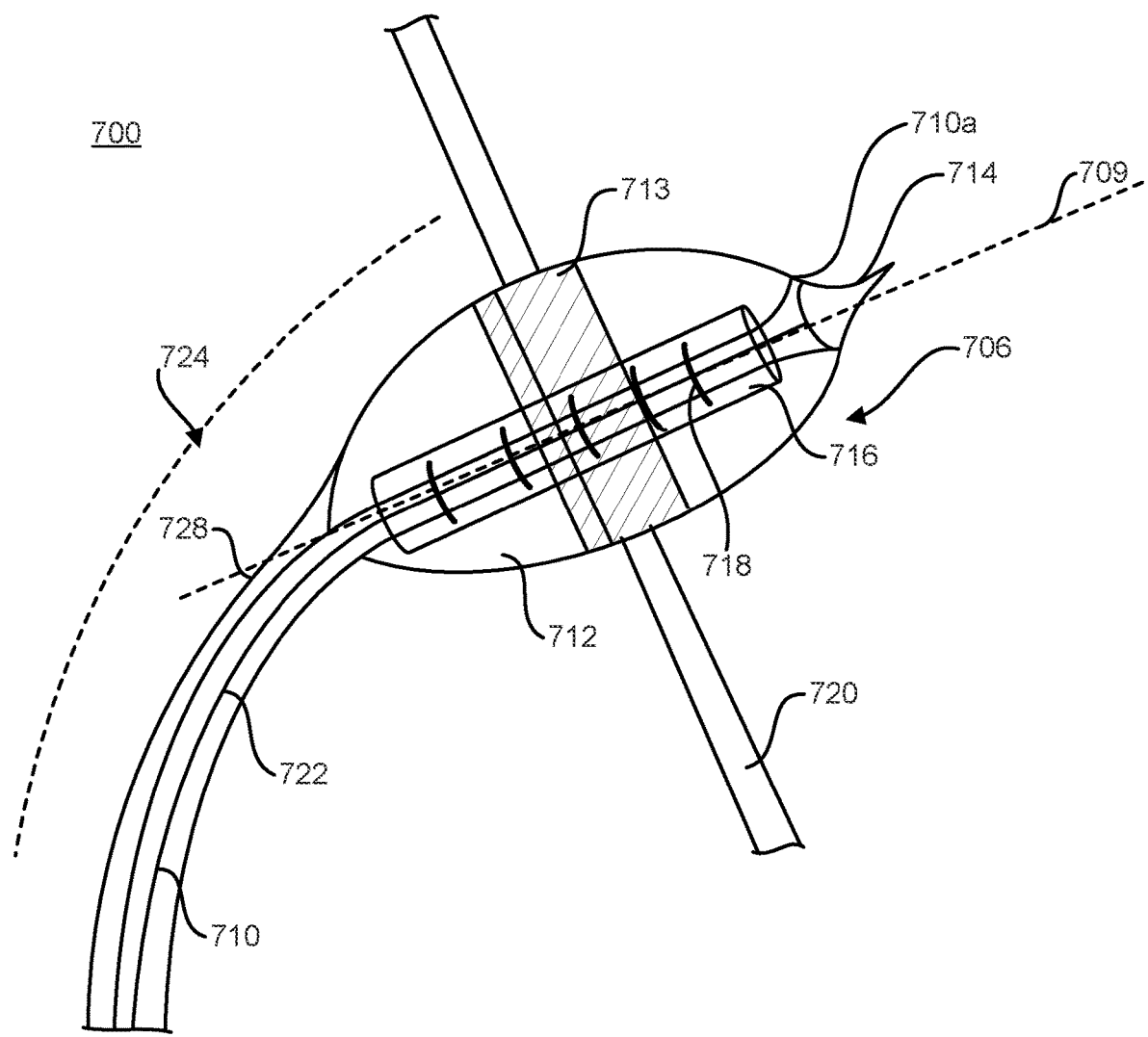
FIG. 7 is a schematic diagram of an example of a shunting catheter, in accordance with embodiments of the present disclosure.

FIG. 7 is a schematic diagram of an example of a shunting catheter 700, in accordance with embodiments of the present disclosure. As shown, the shunting catheter 700 includes a shunting element 706 punctured through a tissue wall 720 (e.g., vessel wall of a patient's CS). The shunting element 706 includes a balloon element 712 and a puncture element 714 disposed on the distal end 710a of a balloon shaft 710. In some embodiments, for example as shown in FIG. 7, the balloon element 712 is expanded and in an inflated state. In certain embodiments, the balloon element 712 includes one or more electrodes 713 disposed on the outer surface of the balloon element 712 where the balloon element 712 contacts the wall 720.

In some embodiments, the shunting element 706 includes a tube 716 (e.g., a hypotube) to support the balloon element 712. The tube 716 may include a plurality of laser cuts 718 generally perpendicular to an axis 709 defined by the shunting element 706. In some instances, the axis 709 is perpendicular to the wall 720. In some instances, the axis 709 is at an angle of about 80 to about 100 degrees to the wall [710] 720.

In some instances, the tube 716 is made of a semi-rigid or rigid material (e.g., stainless steel or nitinol), and may further include a pull wire assembly (not shown) to control the flex or angle of the puncture element 714 relative to the wall 720. As the balloon element 712 is made of expandable and thus relatively flexible material, the tube 716 made of relatively more rigid material disposed in the middle of the balloon element 712 along the axis 709 helps support the shunting element 706 when puncturing through the wall 720 with the puncture element 714. The plurality of laser cuts 718 allows the tube 716 to bend in a certain direction while maintaining rigidity of the shunting element 706 along the axis 709. In some embodiments, the balloon shaft 710 has a preformed curve 722 that includes a radius 724 upon deployment.

In certain embodiments, the shunting catheter 700 further includes a lumen 728 disposed on the outside and surrounding the balloon shaft 710. The lumen 728 may be further disposed inside a catheter shaft (e.g., catheter shaft 502 in FIGS. 5A-B). In some instances, the lumen 728 is configured to control expansion of the balloon element 712. In some examples, the balloon element 712 is in a compressed state (e.g., the compressed state as shown in FIGS. 5A and 6A) during deployment. After the wall 720 is punctured using the needle element 714, the lumen 728 is pulled back such that the balloon element 712 may then be inflated using an inflation source (e.g., the inflation source 122 in FIG. 1) or may be hand inflated by a user based on desired volume or pressure for shunting.

In some instances, the balloon element 712 has a variable size based on its internal pressure after inflation. In some instances, the balloon element 712 has a variable volume based on its internal pressure after inflation. In certain instances, for example during shunting, shunts of various sizes may be created using one balloon. In certain examples, based on a physician or patient's need, a balloon element with variable size and/or volume may be used to create shunts having a diameter of from about 3 mm to about 15 mm, or from about 3 mm to about 12 mm, or from about 3.5 mm to about 12 mm, or from about 4 mm to about 10 mm, or from about 4.5 mm to about 10 mm, or from about 4.5 mm to about 8 mm, or from about 4.5 mm to about 6 mm, or may have a diameter encompassed within these ranges. In some examples, the balloon element may be used to create a shunt having about 5 mm diameter.

In some embodiments, the shunting catheter 700 includes multiple compartments (e.g., lumens) for various elements to provide more targeted control during deployment. For example, besides the lumen 728, the shunting catheter 700 may include additional one or more additional lumens for separately containing functional components such as a guidewire or pull wire assembly. In some examples, the shunting catheter 700 may include additional lumens for holding shunted tissue from a tissue wall.

Figure 8B:
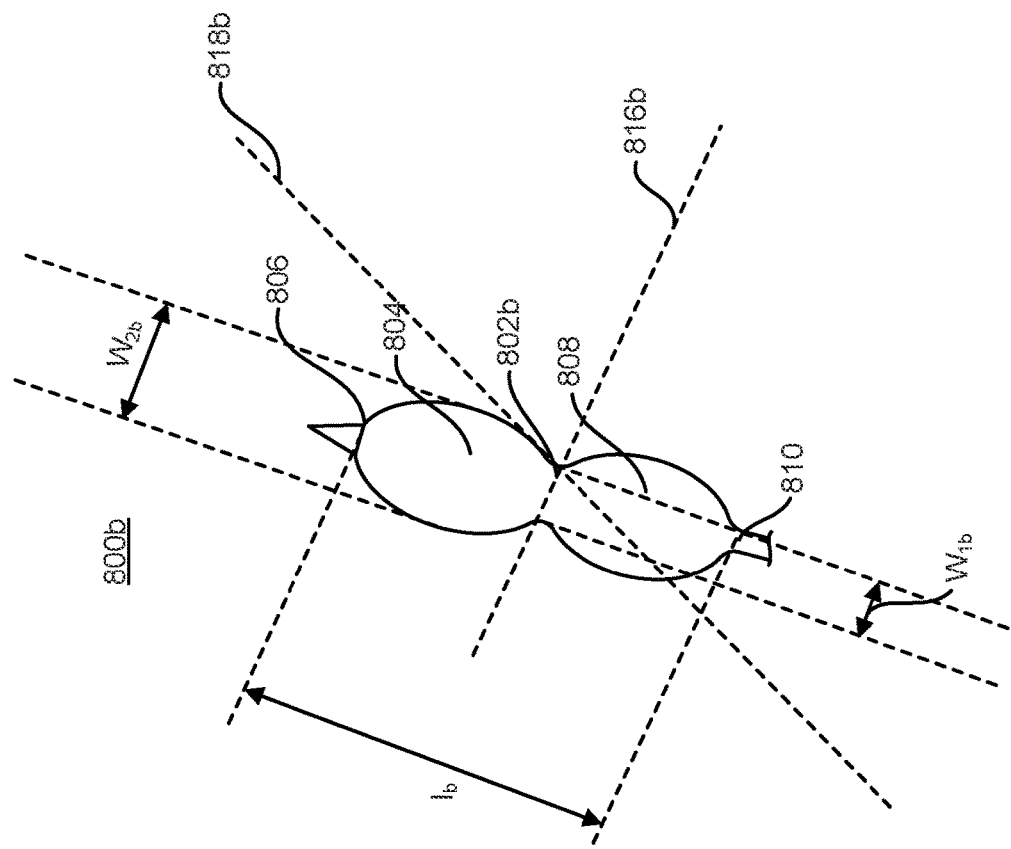
FIGS. 8A-D are schematic diagrams of examples of a balloon element, in accordance with embodiments of the present disclosure.
Figure 8A:
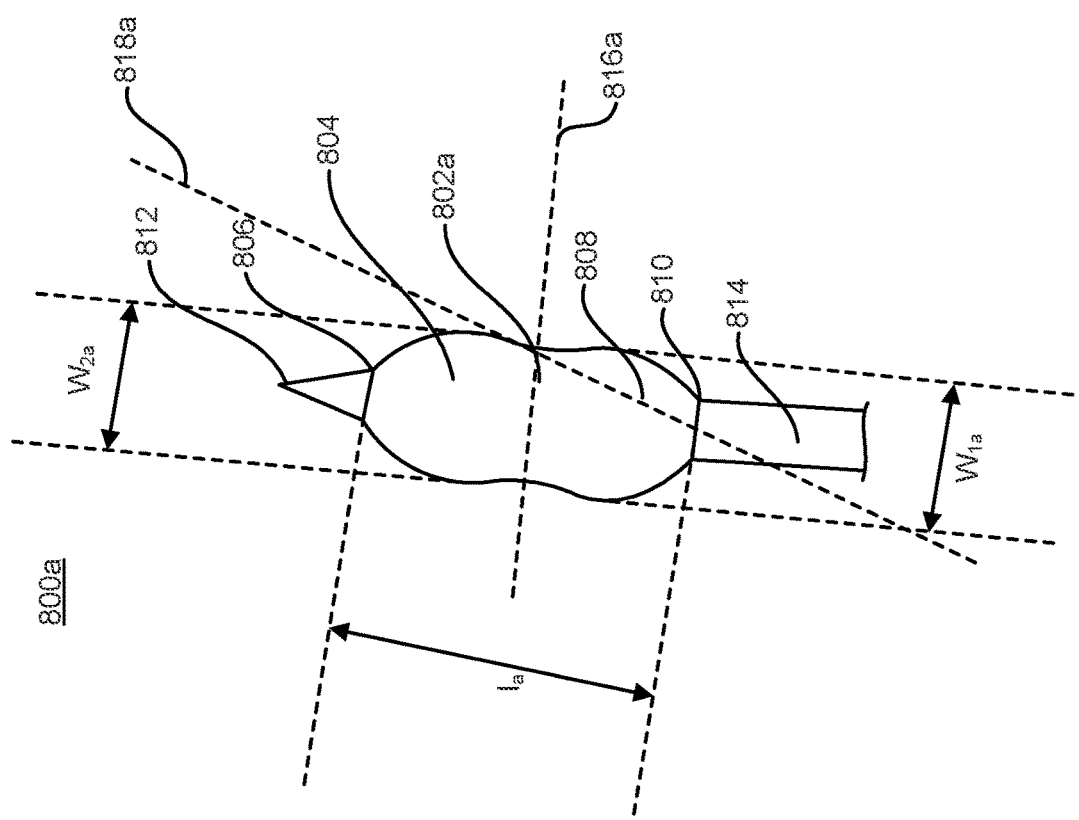

FIGS. 8A-D are schematic diagrams of examples of a balloon element 800a-d, in accordance with embodiments of the present disclosure. As shown in FIG. 8A, a balloon element 800a is in an inflated state including a first section 802a in a middle of the balloon element 800a. In embodiments, the balloon element includes a second section 804 at a distal end 806 of the balloon element 800a and a third section 808 at a proximal end 810 of the balloon element 800a. In some embodiments, the distal end 806 of the balloon element 800a is connected to a puncture element 812, and the proximal end 810 of the balloon element 800a is connected to a balloon shaft 814.

In some embodiments, for example as shown, the first section 802a is between the second section 804 and the third section 808. In some instances, the first section 802a is a narrow section having a diameter smaller than a diameter of the second section 804 or a diameter of the third section 808.

In certain embodiments, the balloon element 800a has a length ($l_a$) from about 4 mm to about 20 mm and varying width along the length of the balloon element 800a. In some instances, the width of the balloon element 800a at the first section ($w_{1a}$) is from about 5 mm to about 15 mm, whereas the width of the balloon element 800a at the second section ($w_{2a}$) is from about 5 mm to about 15 mm, the second section 804 and the third section 808 having the same or similar widths. The ratio of $w_{1a}$ to $w_{2a}$ may be from about 1:5 to 3:5. In some embodiments, a balloon element with a larger width may be used to create a larger opening. In certain embodiments, a balloon element with a variable size and/or volume is used to create shunts of various sizes between a patient's coronary sinus and left atrial. In some instances, a balloon element with a relatively larger width is used to create a shunt with relatively larger size, such that there may be a larger pressure drop in a patient's left atrium as a result of generating the shunt.

A balloon geometry as shown in FIG. 8A may be referred to as a waisted geometry, having a narrow section 802a sandwiched in between two thicker sections. In some embodiments, the first section 802a (e.g., a narrow section) of the balloon element 800a may be referred to as a "seating area", for example, which is intended to host a wall in the cardiovascular system. In certain embodiments, for example during ablation, the first section 802a of the balloon element 800a directly contacts the wall of a patient's vessel, such that the tissue wall surrounds the "seating area" of the balloon 800a. In some instances, a narrow section (e.g., first section 802a) may not be in the center of the balloon element 800a, and may be closer to the distal end 806 or proximal end 810 of the balloon element 800a. In certain instances, an axis 816a goes through a center point of the balloon 800a and is perpendicular to the balloon shaft 814. The first axis 816a is generally located in the middle of the first section 802a of the balloon element 800a. A second axis 818a is defined by the transition between the first section 802a and the second section 804. As shown, the second axis 818a and the first axis 816a forms an angle (e.g., a takeoff angle) of between about 60 degrees to about 85 degrees.

According to some embodiments, the waisted balloon configuration includes several benefits. For example, during deployment and after expanding the balloon element 800a, the position of the balloon element 800a may be further adjusted based on the position of the first section 802 (e.g., the narrow section) relative to a tissue wall (e.g., vessel wall of a patient). In some examples, during shunting, a tissue wall may surround and directly contact the narrow section of the balloon element 800a, thus help stabilize and keep the balloon element 800a in place during shunting.

As shown in FIG. 8B, a balloon element 800b is in an inflated state and having a similar waisted geometry as the balloon element 800a. In some embodiments, the first section 802b is in the middle of the balloon element 800b. In yet some embodiments, a first section (e.g., narrow section) is closer to a proximal end 810 or distal end 806 of the balloon element 800b. In certain instances, an axis 816b goes through a center point of the balloon 800b and is perpendicular to the balloon shaft. The first axis 816b is generally located in the middle of the first section 802b of the balloon element 800b. A second axis 818b is defined by the transition between the first section 802b and the second section 804. As shown, the second axis 818b and the first axis 816b forms an angle (e.g., a takeoff angle) of between about 15 degrees to about 60 degrees. In some embodiments, the angle formed by the second axis 818b and the first axis 816b is smaller than the angle formed by the second axis 818a and the first axis 816a. In certain embodiments, a sharper angle (e.g., a smaller takeoff angle) between the first axis 816a or 816b and a second axis 818a or 818b may help with seating of the balloon 800a-b on the wall of a patient's vessel.

In certain embodiments, the balloon element 800b has a length ($l_b$) from about 4 mm to about 20 mm and varying width along the length of the balloon element 800b. In some embodiments, the first section 802b has a width ($w_{1b}$) of from about 4 mm to about 20 mm, whereas the width of the balloon element 800a at the second section 804 ($w_{2b}$) is from about 4 mm to about 15 mm, the second section 804 and the third section 808 having the same or similar widths. In some instances, the quotient of $w_{1b}$ to $w_{2b}$ is smaller than the quotient of $w_{1a}$ to $w_{2a}$. The ratio of $w_{1b}$ to $w_{2b}$ may be from about 1:5 to about 3:5.

Figure 8D:
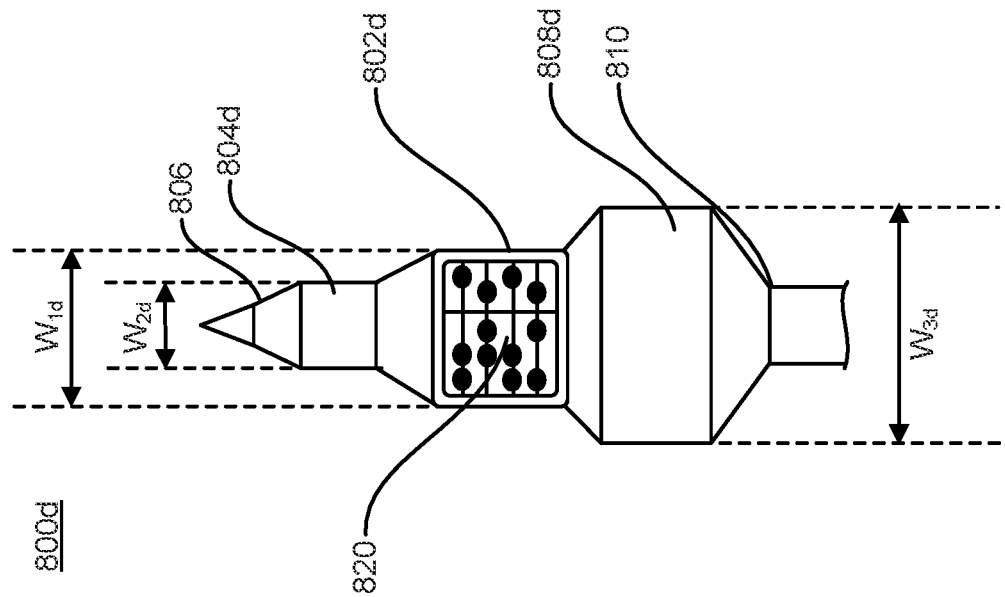
Figure 8C:
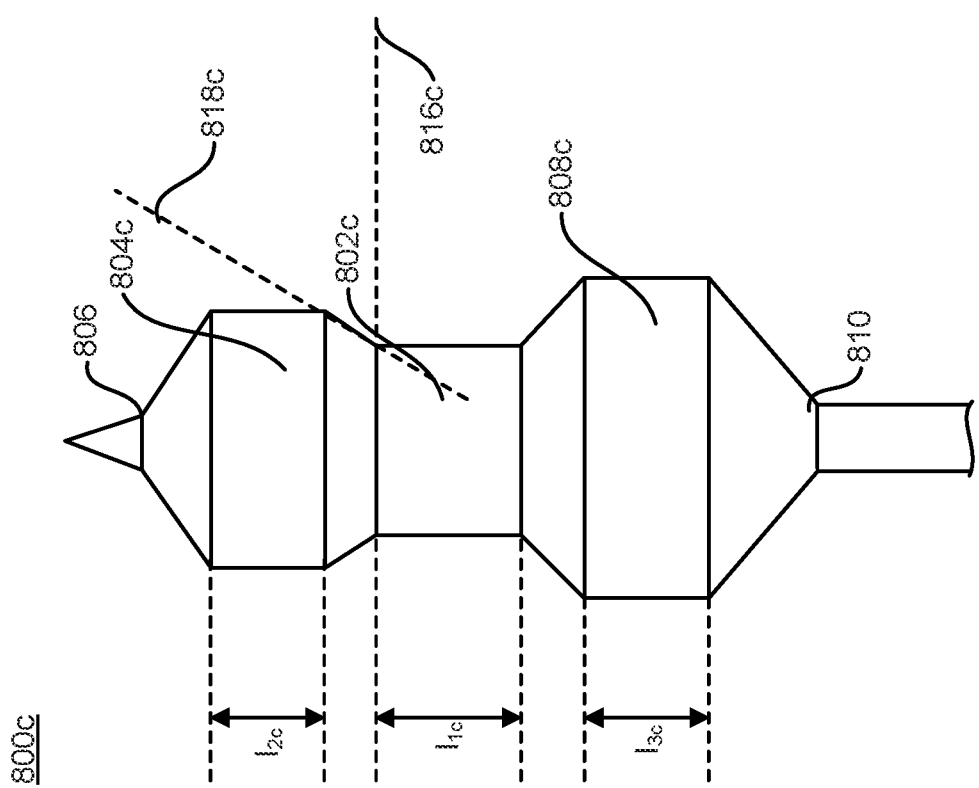

As shown in FIG. 8C, a balloon element 800c is in an inflated state including a first section 802c in the middle of the balloon element 800c. In embodiments, the balloon element 800c includes a second section 804c at a distal end 806 of the balloon element 800c and a third section 808c at a proximal end 810 of the balloon element 800c. In some embodiments, for example as shown, each of the sections 802c, 804c, and 808c includes a straight portion with a constant width, whereas the sections of balloon elements 800a or 800b are of constantly varying width.

A balloon geometry as shown in FIG. 8C may be referred to as a dog bone geometry. In embodiments, the first section 802c has a straight portion with a length ($l_{1c}$) of from about 0.5 mm to about 15 mm, the second section 804c has a straight portion with a length ($l_{2c}$) of from about 4 mm to about 10 mm, and the third section 808c has a straight portion with a length ($l_{3c}$) of from about 1 mm to about 10 mm along the length of the balloon element 800c. In some instances, the first section 802c is the "seating area" of the balloon element 800c, and may have a length that is approximately the same as the thickness of a wall of a patient's vessel. In certain instances, the length of the first section 802c ($l_{1c}$) is from about 0.5 mm to about 4 mm. The lengths of each of the straight portions of sections 802c, 804c, and 808c may be the same or different. In some embodiments, the first section 802c has a smaller width compared to the width of the second section 804c. In some embodiments, the second section 804c has a smaller width compared to the width of the third section 808c.

As shown in FIG. 8D, a balloon element 800d is in an inflated state including a first section 802d in the middle of the balloon element 800d. In embodiments, the balloon element 800d includes a second section 804d at a distal end 806 of the balloon element 800d and a third section 808d at a proximal end 810 of the balloon element 800d. In some embodiments, for example as shown, each of the sections 802d, 804d, and 808d includes a straight portion with a constant width, whereas the sections of balloon elements 800a or 800b are of constantly varying width.

A balloon geometry as shown in FIG. 8D may be referred to as a stepped geometry. In embodiments, the first section 802d has a width ($w_{1d}$) of from about 4 mm to about 15 mm, the second section 804d has a width ($w_{2d}$) of from about 4 mm to about 10 mm, and the third section 808d has a width ($w_{3d}$) of from about 10 mm to about 20 mm. In some embodiments, the second section 804d is further connected to a puncture element 812, and has the smallest width among the three sections. In some embodiments, the first section 802d has a width larger than the width of the second section 804d, but smaller than the width of the third section 808d.

In certain embodiments, one or more electrodes 820 are disposed on the external surface of the balloon 800d surrounding the first section 802d. In certain embodiments, for example during shunting, the electrodes 820 on the first section 802d are configured to deliver energy to ablate tissue surrounding the first section 802d. In some embodiments, having a third section 808d with a larger width than the second section 802d creates a back stop to provide better control of the tissue wall's position and/or movement along the length of the balloon 800d, thus increasing stability of the balloon 800d during shunting.

It is to be understood that the balloon shapes shown in FIGS. 8A-8D are merely examples, and balloons of other shapes or geometry may be used as part of a shunting element of a shunting catheter. In some embodiments, for example, a balloon element may be of a conical shape, a spherical shape, a conical transition to long square shape, a long spherical shape, an offset shape (e.g., balloon partially inflated), a square shape, a conical transition to square shape, a conical transition to long spherical shape, a tapered shape, or a conical transition to offset shape. In certain embodiments, the balloon element is symmetrical along the length of the balloon shaft. In yet certain embodiments, for example for the offset shape, the balloon element is asymmetrical along the length of the balloon shaft.

FIGS. 9A-D are examples of cross-section view 900a-d of a balloon element, in accordance with embodiments of the present disclosure. In some embodiments, a balloon element has a cross-sectional shape perpendicular to the balloon element shaft, the cross-sectional shape being circular, oval, or substantially square or rectangular with rounded corners. In certain embodiments, during shunting, different cross-sectional shape of the balloon element results in different shapes of the shunt created. As such, the geometry of a shunt may be the same or similar to the cross-sectional shape of the balloon element. In some examples, the cross section of a balloon element has an asymmetrical cross-sectional shape (e.g., an offset shaped balloon) configured to create a shunt that is also of asymmetrical shape.

According to some embodiments, for example as shown in FIG. 9A, the cross section 900a of a balloon element is of a circular shape. According to certain embodiments, for example as shown in FIG. 9B, the cross section 900b of a balloon element is of an oval shape. In some embodiments, for example as shown in FIG. 9C, the cross section 900c of a balloon element is of a substantially square shape with one or more rounded corners 902. In certain embodiments, for example as shown in FIG. 9D, the cross section 900d of a balloon element is of a substantially rectangular shape with one or more rounded corners 904.

In some embodiments, balloon elements with non-circular cross sectional shape may have one or more benefits for ablation. For example, a balloon element with an oval or rectangular cross sectional shape may help provide sufficient area for blood flow within the size of the vessel (e.g., the CS of a patient). In some instances, a balloon element with an oval or rectangular cross sectional shape provides flexibility with generating a shunt of a desired shape and/or diameter. For example, a shunt along the vessel flowing direction may be generated in a patient's vessel with a smaller width by using a balloon element with an oval cross sectional shape.

Figure 10A:
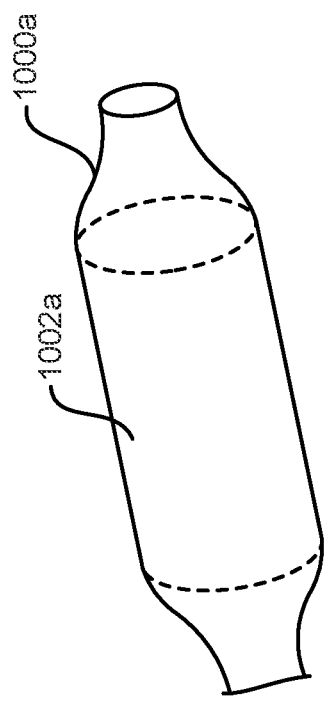

FIGS. 10A-I are schematic diagrams of examples of electrode configurations placed on a balloon element 1000a, according to certain embodiments of the present disclosure. As shown in FIGS. 10A, the balloon element 1000a has a long spherical shape, and a film 1002a is disposed on the external surface of the balloon element 1000a. One or more electrodes may be disposed on the film 1002a before the film 1002a is placed on the balloon element 1000a. In some embodiments, electrodes are placed on the surface of the balloon element 1000a before being covered with the film 1002a. In certain embodiments, the electrodes are configured to deliver energy to the surrounding tissue, and may include platinized titanium anodes, platinum wire, iridium wire, nitinol, stainless steel, cobalt chromium, gold, copper, metal encapsulated with a silicone sheet, or a combination thereof.

Figure 10B:
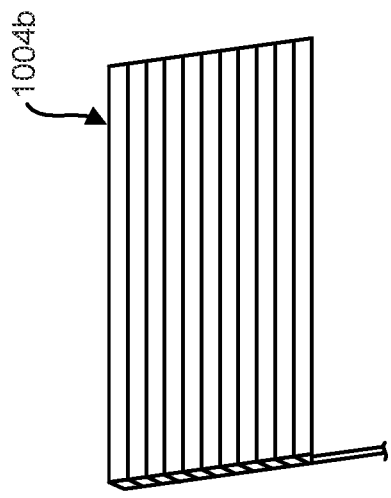
Figure 10D:
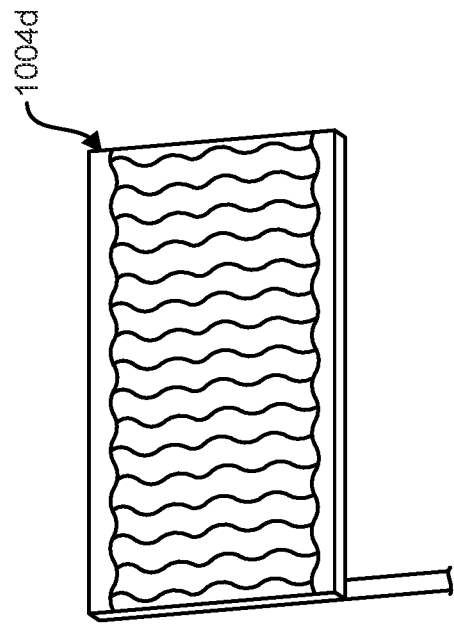
Figure 10C:
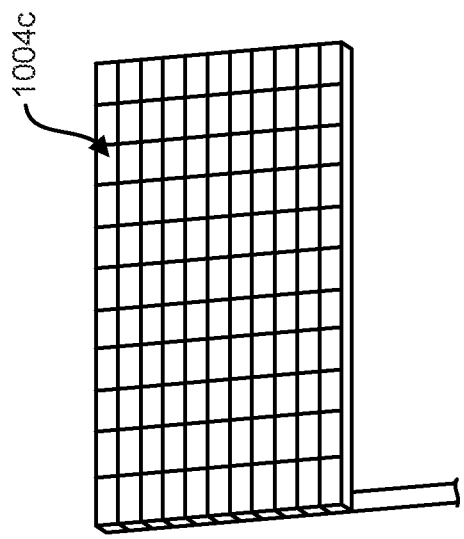

As shown in FIGS. 10B-D, the one or more electrodes 1004b-d have a variety of configurations. In some embodiments, for example as shown in FIG. 10B, the electrode 1004b is of a lined pattern. In some embodiments, for example as shown in FIG. 10C, the electrode 1004c is of a grid pattern. In some embodiments, for example as shown in FIG. 10D, the electrode 1004d is in the form of curved lines. In certain embodiments, the grid pattern of the electrode 1004c and the curved lines of electrode 1004d may reduce the strain on electrodes during shunting. In some embodiments, the grid pattern of the electrode 1004c and the curved lines of electrode 1004d may reduce the strain on electrodes during crimping of the balloon element 1000a.

As shown in FIGS. 10e-h, electrodes 1004e-h are placed individually and directly on the surface of the balloon element 1000e-h without a film. In some embodiments, for example as shown in FIG. 10E, electrodes 1004e are directly placed on the surface of the balloon element 1000e having a straight lined shape. In some embodiments, for example as shown in FIG. 10F, electrodes 1004f are directly placed on the surface of the balloon element 1000f, and further include a plurality of individual electrodes 1006f having a thickness of about 100 microns and protruding from the surface of the balloon element 1000f. In certain embodiments, for example as shown in FIG. 10G, electrodes 1004g has a curved pattern. In some instances, when electrodes are formed in a curved pattern, the effect of any potential deformation of the shape of the balloon element 1000g may be decreased by decreasing potential change in the strength and shape of electric field surrounding the balloon element 1000g.

According to certain embodiments, for example as shown in FIG. 10H, the balloon element 1000h includes a narrow section 1006h in the middle surrounded by sections 1008h and 1010h on the two ends of the balloon element 1000h. In certain embodiments, the balloon element 1000h further include electrodes 1004h having straight sections 1012h and curved sections 1014h and 1016h on the two ends of the balloon element 1000h.

Figure 10I:
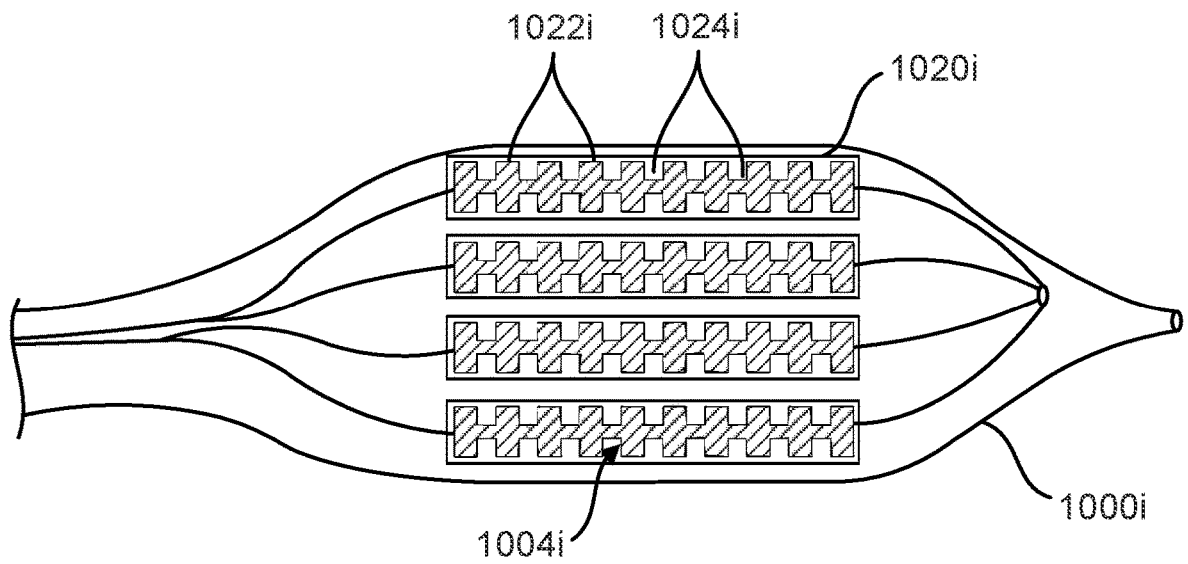

According to certain embodiments, for example as shown in FIG. 10I, balloon element 1000i includes electrodes 1004i. Although only four electrodes 1004i are depicted in the example of FIG. 10I, any number of electrodes 1004i may be disposed on balloon element 1000i. In certain instances, balloon element 1000i may include six, eight, or ten electrodes 1004i. In some embodiments, one or more electrodes of electrodes 1004i have a longitudinal center portion 1020i and a plurality of protrusions 1022i extended from the center portion 1020i. In certain embodiments, at least a part of the plurality of protrusions 1022i are perpendicular to the longitudinal center portion 1020i. In certain embodiments, at least a part of the plurality of protrusions 1022i are parallel to one another. In some instances, each of the plurality of protrusions 1022i are parallel to one another.

According to certain embodiments, for example, as shown in FIG. 10I, electrodes 1004i may include portions of nonconductive material 1024i between each protrusion of the plurality of protrusions 1022i. In some embodiments, the protrusions 1022i are made of conductive material, and surrounded by the nonconductive material 1024i. Heat may be transmitted along the edges of electrodes 1004i near the nonconductive material 1024i. In certain instances, the nonconductive material 1024i extends towards center portion 1020i. As such, heat may be generated not only at the edges of electrodes 1004i furthest away from center portion 1020i, but also along the edges of the plurality of protrusions 1022*i* between each of the plurality of protrusions 1022*i*. This may allow electrodes 1004*i* to provide more uniform tissue ablation.

Figure 11:
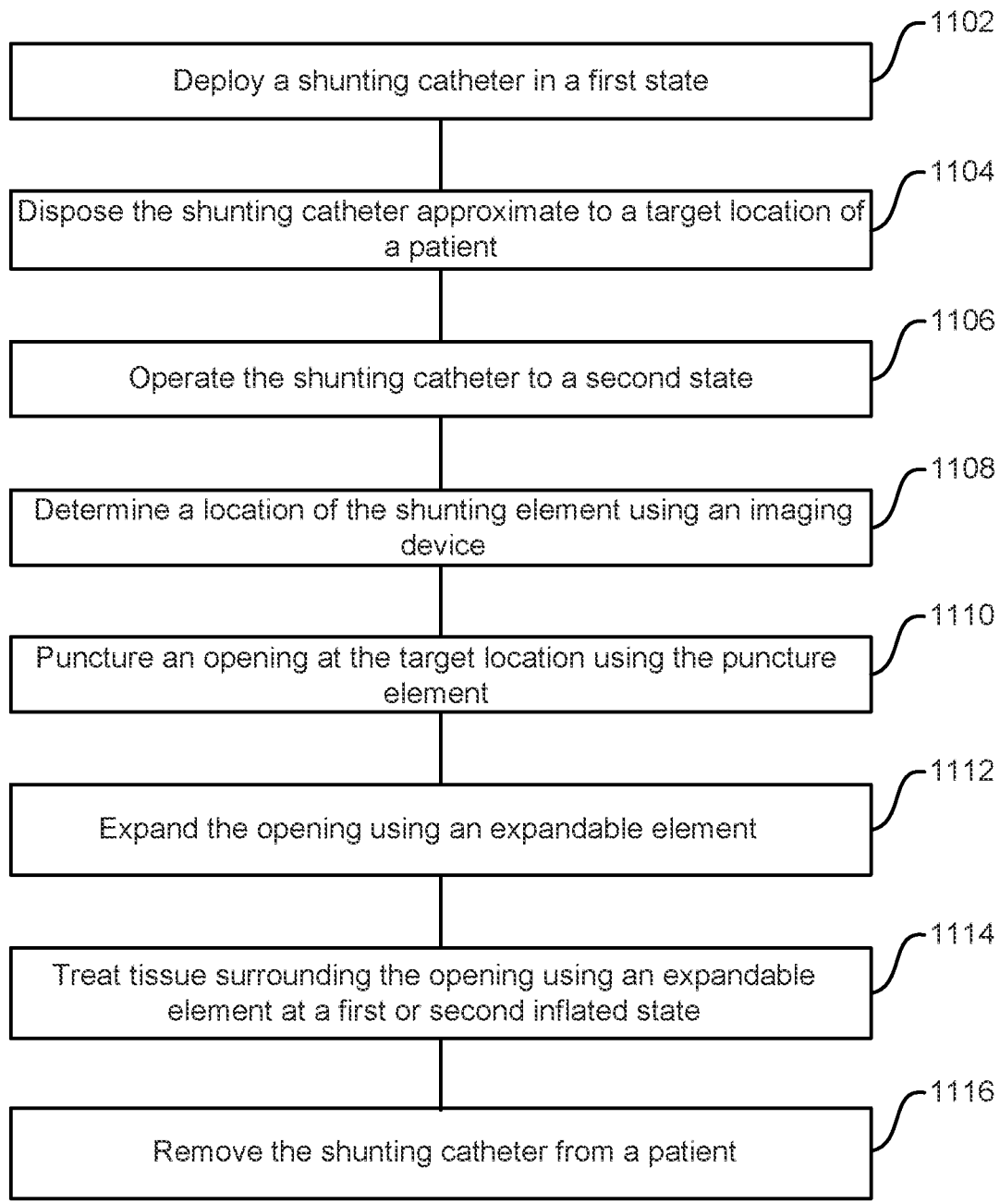
FIG. 11 is a flow diagram illustrating a process of creating a shunt in a patient, in accordance with embodiments of the present disclosure.

FIG. 11 is a flow diagram illustrating a process 1100 of creating a shunt in a patient, in accordance with embodiments of the present disclosure. Aspects of embodiments of the process 1100 may be performed, for example, by a shunting catheter system or a controller (e.g., the system 104 in FIG. 1, the controller 112 in FIG. 1). One or more steps of the process 1100 are optional and/or can be modified by one or more steps of other embodiments described herein. Additionally, one or more steps of other embodiments described herein may be added to the process 1100. In some embodiments, the shunt may be formed in a coronary sinus of a patient. In certain embodiments, the shunt includes an opening between a patient's coronary sinus and left atrium.

At step 1102, in some embodiments, the process 1100 includes deploying a shunting catheter in a first state, the shunting catheter including a catheter shaft having a distal end and a proximal end and a shaft lumen, a shunting element having a proximal end and a distal end, and a puncture element disposed proximate to the distal end of the shunting element. In some embodiments, the shunting element is disposed in the shaft lumen at the first state. In certain embodiments, the catheter shaft has a shaft opening, and the shunting element extends from the catheter shaft through the shaft opening. In certain embodiments, deploying the shunting catheter includes inserting the shunting catheter through a superior vena cava of a patient into a coronary sinus of the patient. In certain embodiments, deploying the shunting catheter includes inserting the shunting catheter through an inferior vena cava of a patient into a coronary sinus of the patient.

At step 1104, the process 1100 includes disposing the shunting catheter approximate to a target location of a patient. At step 1106, the process 1100 includes operating the shunting catheter to a second state, for example, the shunting element extends from the catheter shaft at an angle greater than zero degree at the proximal end of the shunting element at the second state. In some embodiments, the shunting catheter includes an apposition element disposed proximate to the shunting element, and the apposition element is protruded from the catheter shaft at the second state. In certain embodiments, the catheter shaft has a shaft opening, and the shunting element extends from the catheter shaft through the shaft opening.

At step 1108, the process 1100 may include determining a location of the shunting element using an imaging device. In some embodiments, the imaging device includes one or more visualization elements disposed proximate the shunting element.

At step 1110, the process 1100 includes puncturing, using the puncture element, an opening at the target location. In some embodiments, the target location is at a coronary sinus of a patient. At 1112, the process 1100 includes expanding the opening using the expandable element (e.g., the expandable element 312 in FIG. 3).

At step 1114, the process 1100 includes treating tissue (e.g., by ablating, displacing, burning, or shrinking the tissue) surrounding the opening using an expandable element at a first or second inflated state. In some embodiments, the shunting element includes an expandable element (e.g., a balloon) disposed at the distal end of the shunting element. In certain embodiments, the expandable element has a plurality of states including a compressed state, a first inflated state, and a second inflated state. In some instances, the balloon is expanded at the second state and configured to deliver energy (e.g., ablative energy, radiofrequency (RF) energy, phased RF energy, thermal energy, cryogenic energy, pulse ablative energy (e.g., pulsed field ablation (PFA)), microwave energy, laser energy, ultrasound energy, etc.) to the tissue surrounding the opening.

At step 1116, the process 1100 may include removing the shunting catheter from a patient. In some embodiments, the process 1100 may include removing the shunting catheter, which includes removing the catheter shaft, the puncture element, and the shunting element. In certain embodiments, the process 1100 does not leave any implant device at the target location. In some embodiments, a shunt is formed by creating an opening between a coronary sinus and a left atrium of a patient. In certain embodiments, the shunting catheter is removed from the coronary sinus of the patient. In certain embodiments, the formed shunt is an opening that does not include an implant (e.g., a frame or structure to support an opening). In some embodiments, the shunt consists of an opening between the coronary sinus and the left atrium of a patient; where the shunt does not include an implant.

According to some embodiments, the process 1100 includes generating a shunt using a shunting element of a shunting catheter. In certain embodiments, the shunt includes an expanded opening between the coronary sinus and left atrium of a patient. In some embodiments, the shunt does not include any implant.

Figure 12:
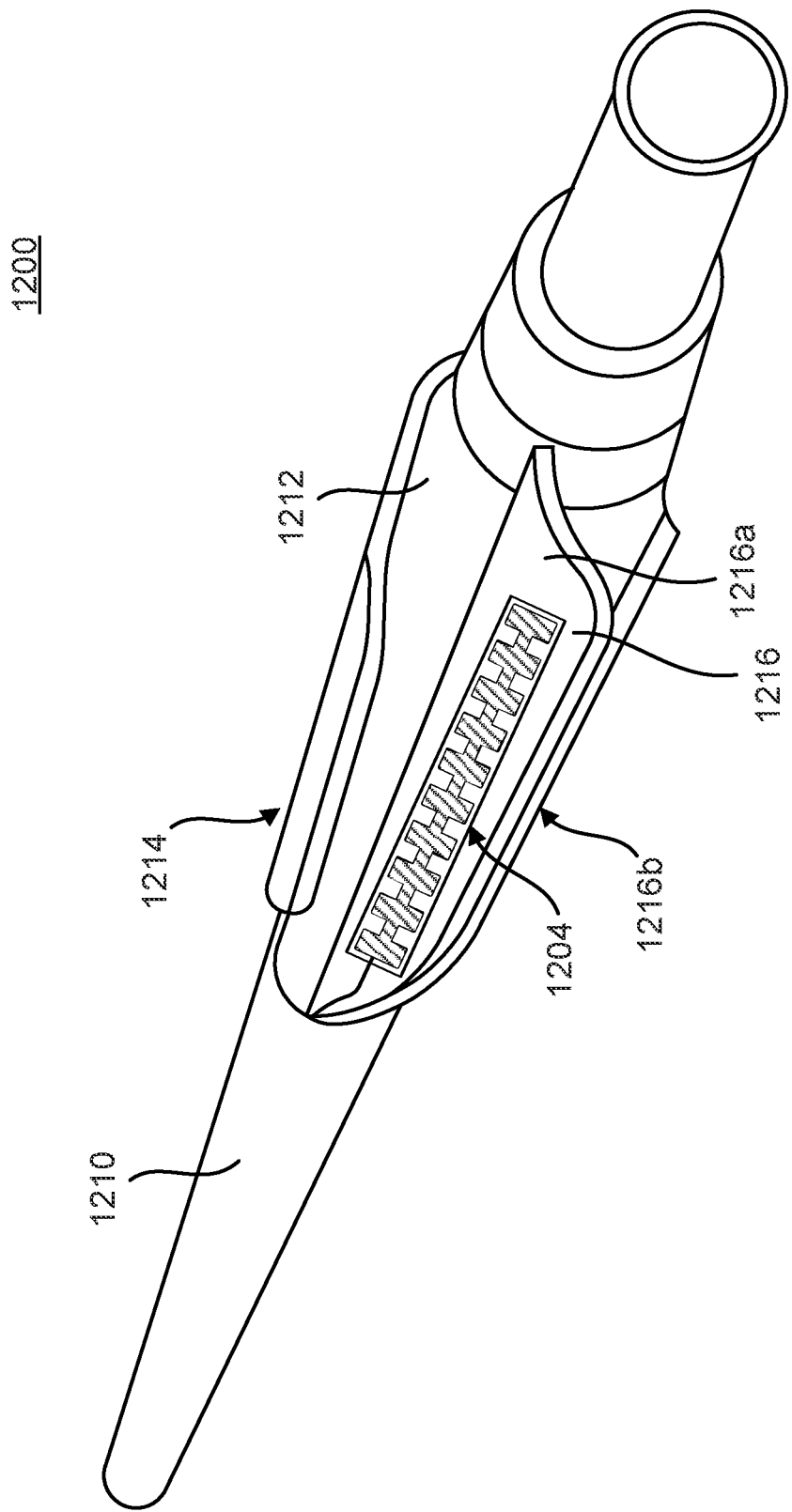
FIG. 12 is a schematic diagram of a perspective view of an example of a shunting element, in accordance with embodiments of the present disclosure.

FIG. 12 is a schematic diagram of a perspective view of an example of a shunting element 1200, in accordance with embodiments of the present disclosure. As shown, the shunting element 1200 includes a balloon element 1212 disposed on the distal end of a balloon shaft 1210. According to certain embodiments, the balloon element 1212 includes a membrane made of material including nylon, copolymers of polyamide and polyether, polyethylene terephthalate (PET), polyurethane (PU), silicone, thermoplastic polyurethanes, polyamides, or a combination thereof.

According to some embodiments, the balloon element 1212 includes a plurality of states. In some embodiments, for example as shown in FIG. 12, the balloon element 1212 is crimped and in a compressed state. In some instances, for example as shown in FIG. 12, the balloon element 1212 is in a compressed state having a pleated configuration, where the balloon element 1212 is crimped into one or more flat pieces (e.g., one or more pleats 1214) that are folded over each other. In some instances, each pleat of the one or more pleats 1214 may be of the same size and thickness. In some instances, each pleat of the one or more pleats 1214 may include one or more pleating surfaces 1216. In some instances, each pleat of the one or more pleats 1214 may include a first pleating surface 1216*a* on a first side of the pleat, and a second pleating surface 1216*b* on a second side of the pleat, where the second side is opposing to the first side.

In some embodiments, one electrode of the plurality of electrodes 1204 is disposed entirely on a pleating surface on one side of one of the pleats of the one or more pleats 1214. As such, the potential for the one electrode to bend or fold while attached to balloon element 1212 in the compressed state may be reduced, decreasing the likelihood of damage to the electrodes 1204. In some instances, the one electrode of the plurality of electrodes 1204 that is disposed entirely on the pleating surface is disposed on an external surface of the one pleat of the one or more pleats 1214. For example, the electrode may be disposed on the surface of the one pleat that faces outward from the balloon shaft 1210. In some instances, the one electrode of the plurality of electrodes 1204 that is disposed entirely on the pleating surface is disposed on a surface of the one pleat of the one or more pleats 1214 that is facing towards the balloon shaft 1210.

In some embodiments, a number of electrodes 1204 may be disposed entirely on a number of pleating surfaces 1216 of the one or more pleats 1214, respectively. In some instances, at least one electrode of the plurality of electrodes 1204 is disposed entirely on each of the one or more pleats 1214 (e.g., disposed on a pleating surface of the one or more pleats 1214). In some instances, each of or a part of one or more electrodes of the plurality of electrodes 1204 is disposed entirely on a respective pleating surface of the one or more pleating surfaces 1216.

Figure 13:
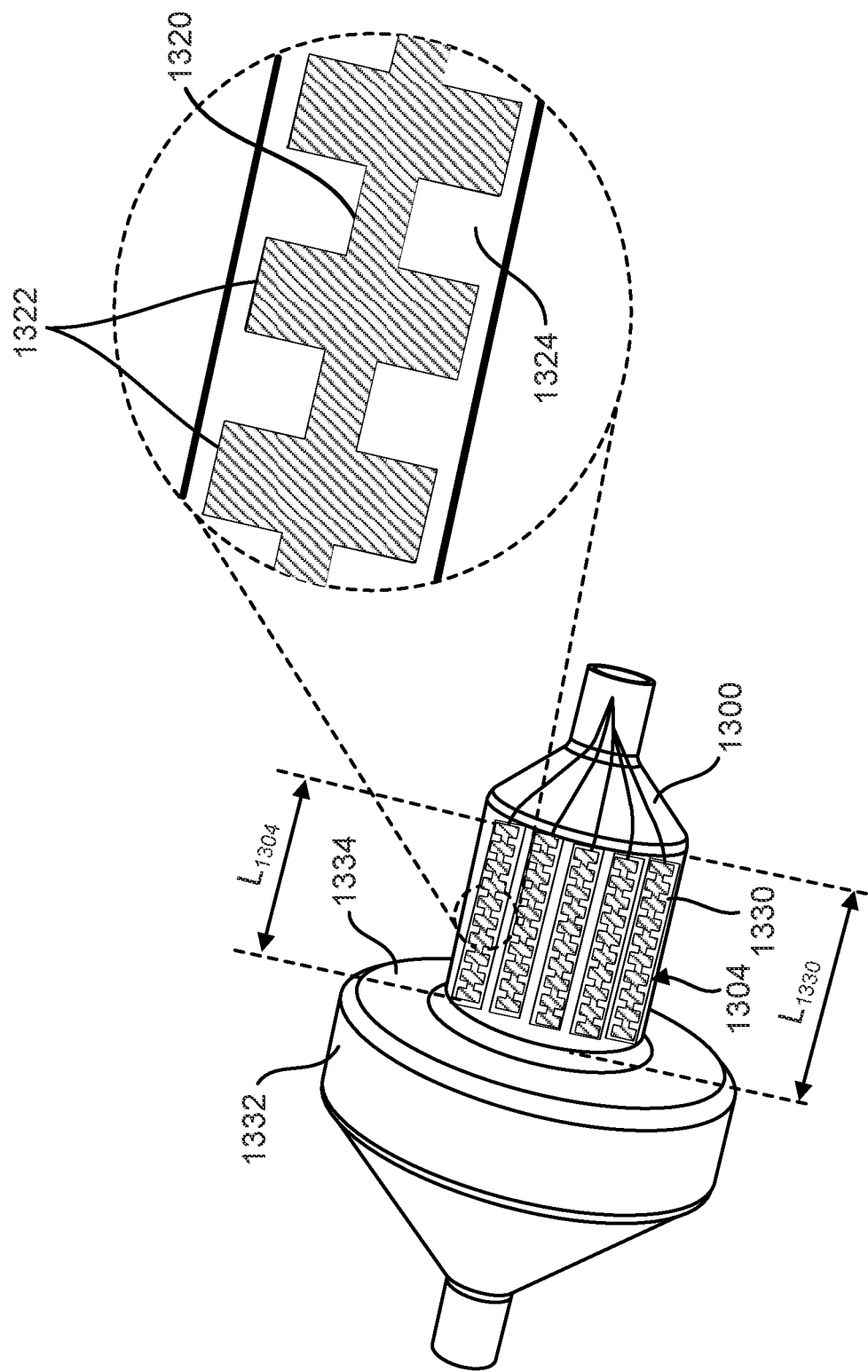
FIG. 13 is a schematic diagram of an example expandable element, in accordance with embodiments of the present disclosure.

FIG. 13 is a schematic diagram of an example expandable element (e.g., balloon element 1300), in accordance with embodiments of the present disclosure. The balloon element 1300 includes an anchor component 1332 and a shunting component 1330. In certain embodiments, the balloon element 1300 further includes one or more electrodes 1304 disposed on the shunting component 1330. Although only five electrodes 1304 are depicted in the example of FIG. 13, any number of electrodes 1304 may be disposed on the shunting component 1330. In some instances, the one or more electrodes 1304 include a longitudinal length ($L_{1304}$) that is substantially equal to a longitudinal length ($L_{1330}$) of shunting component 1330. In certain instances, the one or more electrodes 1304 include a longitudinal length $L_{1304}$ that is slightly shorter than a longitudinal length $L_{1330}$ of shunting component 1330. In some instances, the longitudinal length $L_{1304}$ of the one or more electrodes 1304 may be in a range of from about 70% to about 100%, or from about 80% to about 100%, or from about 90% to about 100% of the longitudinal length $L_{1330}$ of the shunting component 1330.

In some embodiments, the one or more electrodes 1304 have a longitudinal center portion 1320 and a plurality of protrusions 1322 extended from the center portion 1320. In certain embodiments, at least a part of the plurality of protrusions 1322 are perpendicular to the longitudinal center portion 1320. In certain embodiments, at least a part of the plurality of protrusions 1322 are parallel to one another. In some instances, each of the plurality of protrusions 1322 are parallel to one another.

According to certain embodiments, for example, as shown in FIG. 13, the one or more electrodes 1304 may be surrounded by nonconductive material 1324 (e.g., electrode backing), including portions of nonconductive material between each protrusion of the plurality of protrusions 1322. Heat may be generated along the edges of electrodes 1304 near the nonconductive material 1324. Because the nonconductive material 1324 extends towards center portion 1320, heat may be generated not only at the edges of electrodes 1304 furthest away from center portion 1320, but also along the edges of the plurality of protrusions 1322 between each of the plurality of protrusions 1322. This may allow electrodes 1304 to provide more uniform tissue ablation.

In some instances, the balloon element 1300 is in a compressed state at a first state of the shunting element (e.g., during deployment). In some instances, the balloon element 1300 is in a compressed state when a puncture element is used to puncture through a tissue wall. In some embodiments, the balloon element 1300 is expanded to an inflated state at a second state of the shunting element (e.g., during shunting). In some instances, the balloon element 1300 is expanded to an inflated state from a compressed state after the puncture element punctures through a tissue wall.

In some embodiments, the balloon element 1300 may be expanded to a first inflated state, for example, the anchor component 1332 being inflated and the shunting component 1330 being deflated (e.g., not inflated). In some embodiments, for example as shown in FIG. 13, the balloon element 1300 is expanded to a second inflated state (e.g., a fully inflated state), for example, both the anchor component 1332 and the shunting component 1330 both being inflated. In some embodiments, when balloon element 1300 is fully inflated (e.g., in a second inflated state), the anchor component 1332 has a first diameter, and the shunting component 1330 has a second diameter, wherein the first diameter is larger than the second diameter. In some instances, the first diameter of the anchor component 1332 may be in the ranges of 4 millimeters to 16 millimeters at the first inflated state. In some examples, the anchor component 1332 has a diameter in the ranges of 4 millimeters to 20 millimeters at the second inflated state. In some instances, the difference between the diameter of the anchor component 1332 (e.g., the first diameter) and the diameter of the of the shunting component 1330 (e.g., the second diameter) is larger than about 1 mm, or larger than about 1.5 mm, or larger than about 2 mm, or larger than about 2.5 mm, or larger than about 3 mm, or larger than about 3.5 mm, or larger than about 4 mm, or larger than about 4.5 mm, or larger than about 5 mm, or larger than about 6 mm, or larger than about 8 mm, or larger than about 10 mm, or larger than about 12 mm, or larger than about 14 mm, or larger than about 16 mm.

In some embodiments, the anchor component 1332 is configured to facilitate the placement of balloon element 1300 within a patient (e.g., at a target location of a vessel or anatomy). In some embodiments, the balloon element 1300 is expanded to an inflated state (a first inflated state and/or a second inflated state) from a compressed state after the puncture element punctures through a tissue wall (e.g., the vessel wall of a patient's CS). The diameter of the anchor component 1332, when expanded to an inflated state, may be substantially larger than the diameter of the puncture hole through the tissue wall, such that as the balloon element 1300 is pulled back through the puncture hole, the anchor component 1332 is configured to pull back the tissue wall. In some instances, the diameter of the anchor component 1332 is large enough to pull back the tissue wall when the anchor component 1332 is in the first inflated state. In some instances, the diameter of the anchor component 1332 is large enough to pull back the tissue wall when the anchor component 1332 is in the second inflated state. The position of the balloon element 1300 may be fixed with respect to the tissue wall when the anchor component 1332 pulls back the tissue wall.

In some embodiments, a proximal surface 1334 of the anchor component 1332 may be angled, when the anchor component 1332 is inflated, to fix the balloon element 1300 within the patient. The proximal surface 1334 may catch on the tissue wall without expanding a puncture hole in the tissue wall. In some examples, as shown in FIG. 13, the proximal surface 1334 may define a plane perpendicular to a longitudinal axis of the balloon element 1300. In some instances, the proximal surface 1334 may angle towards a proximal direction (e.g., the angle between a longitudinal axis of the balloon element 1300 and the proximal surface 1334 on a proximal side of the proximal surface 1334 may be less than 90 degrees). In yet some instances, the proximal surface 1334 may angle towards a distal direction (e.g., the angle between a longitudinal axis of the balloon element 1300 and the proximal surface 1334 on a proximal side of the proximal end 1334 may be larger than 90 degrees). In some embodiments, the proximal surface 1334 of the anchor component 1332 may not form a uniform or constant angle relative to the longitudinal axis of the balloon element 1300. In certain embodiments, the anchor component 1332 may have a "canted" shape with a portion of the proximal surface 1334 forming an acute angle relative to the longitudinal axis of the balloon element 1330 and another portion of the proximal surface 1334 forming an obtuse angle relative to the longitudinal axis of the balloon element 1330.

In some embodiments, the shunting component 1330 and the anchor component 1332 may share an interior lumen such that both the shunting component 1330 and the anchor component 1332 are simultaneously inflated. In some instances, when the anchor component 1332 is inflated to a first inflated state, the shunting component 1330 may be inflated to a first inflated state. The diameter of the anchor component 1332 in the first inflated state may be larger than the diameter of the shunting component 1330 in the first inflated state. In some instances, when the anchor component 1332 is inflated at a second inflated state, the shunting component 1330 may be inflated to a second inflated state. The diameter of the anchor component 1332 in the second inflated state may be larger than the diameter of the shunting component 1330 in the second inflated state.

The diameter of shunting component 1330 may be sized to provide shunting of the tissue wall when balloon element 1300 is in an inflated state (e.g., a first inflated state and/or a second inflated state). In some instances, after the balloon element 1300 is expanded, as shown in FIG. 13, energy (e.g., ablative energy, radiofrequency (RF) energy, phased RF energy, thermal energy, cryogenic energy, pulse ablative energy (e.g., pulsed field ablation (PFA)), microwave energy, laser energy, ultrasound energy, etc.) may be delivered to the one or more electrodes 1304 disposed on the shunting component 1330 to ablate tissue surrounding the shunting component 1330.

Figure 14:
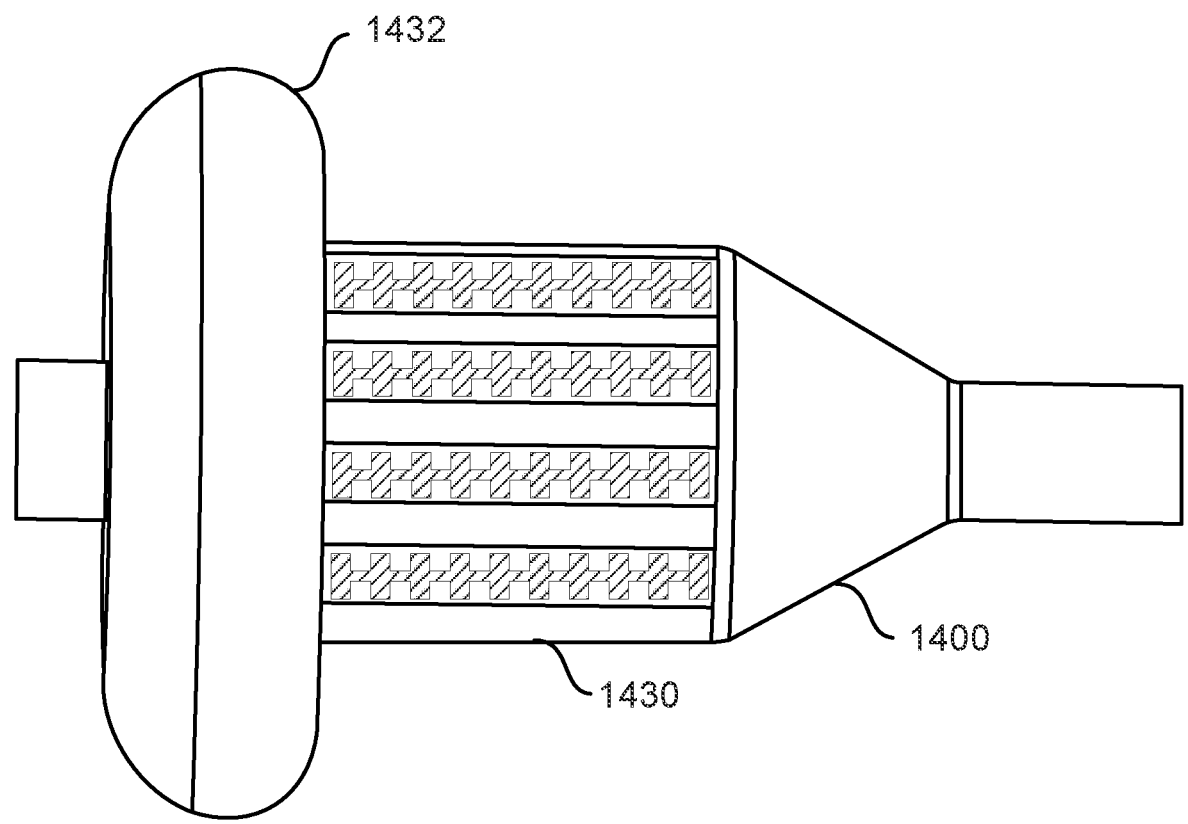
FIG. 14 is a schematic diagram of an example expandable element, in accordance with embodiments of the present disclosure.

FIG. 14 is a schematic diagram of an example expandable element (e.g., balloon element 1400), in accordance with embodiments of the present disclosure. The balloon element 1400 includes an anchor component 1432 and a shunting component 1430.

In some embodiments, the balloon element 1400 may be expanded to a first inflated state, for example, the anchor component 1432 being inflated and the shunting component 1430 being deflated (e.g., not inflated). In some embodiments, for example as shown in FIG. 14, the balloon element 1400 is expanded to a second inflated state (e.g., a fully inflated state), for example, both the anchor component 1432 and the shunting component 1430 both being inflated. In some embodiments when balloon element 1400 is fully inflated (e.g., in a second inflated state), anchor component 1432 has a first diameter, and shunting component 1430 has a second diameter, wherein the first diameter is larger than the second diameter. In some instances, the difference between the diameter of the anchor component 1432 (e.g., the first diameter) and the diameter of the of the shunting component 1430 (e.g., the second diameter) is larger than about 1 mm, or larger than about 1.5 mm, or larger than about 2 mm, or larger than about 2.5 mm, or larger than about 3 mm, or larger than about 3.5 mm, or larger than about 4 mm, or larger than about 4.5 mm, or larger than about 5 mm, or larger than about 6 mm, or larger than about 8 mm, or larger than about 10 mm, or larger than about 12 mm, or larger than about 14 mm, or larger than about 16 mm.

In some embodiments, the anchor component 1432 is configured to facilitate the placement of balloon element 1400 within a patient (e.g., at a target location of a vessel or anatomy). In some embodiments, the balloon element 1400 is expanded to an inflated state (a first inflated state and/or a second inflated state) from a compressed state after the puncture element punctures through a tissue wall. The diameter of the anchor component 1432, when expanded to an inflated state, may be substantially larger than the diameter of the puncture hole through the tissue wall, such that as the balloon element 1400 is pulled back through the puncture hole, the anchor component 1432 is configured to pull back the tissue wall. In some instances, the diameter of the anchor component 1432 is large enough to pull back the tissue wall when the anchor component 1432 is in the first inflated state. In some instances, the diameter of the anchor component 1432 is large enough to pull back the tissue wall when the anchor component 1432 is in the second inflated state. The position of the balloon element 1400 may be fixed with respect to the tissue wall when anchor component pulls back the tissue wall.

In some embodiments, balloon element 1400 is a multi-balloon element composed of multiple separately inflatable balloons. In some instances, balloon element 1400 may be a dual balloon, wherein the anchor component 1432 is a first balloon and the shunting component 1430 is a second balloon. The first balloon and second balloon may not share a lumen, such that the anchor component 1432 and the shunting component 1430 are inflatable independent of one another.

In some instances, when the anchor component 1432 is inflated to a first inflated state, the shunting component 1430 may be configured to remain deflated. In some instances, when the anchor component 1432 is inflated to a first inflated state, the shunting component 1430 may be inflated to a first inflated state. In some instances, when the anchor component 1432 is inflated to a first inflated state, the shunting component 1430 may be inflated to a second inflated state. In some instances, when the anchor component 1432 is inflated to a second inflated state, the shunting component 1430 may be configured to remain deflated. In some instances, when the anchor component 1432 is inflated to a second inflated state, the shunting component 1430 may be inflated to a first inflated state. In some instances, when the anchor component 1432 is inflated to a second inflated state, the shunting component 1430 may be inflated to a second inflated state. In some instances, when the shunting component 1430 is inflated to a first inflated state, the anchor component 1432 may remain deflated. In some instances, when the shunting component 1430 is inflated to a second inflated state, the anchor component 1432 may remain deflated.

According to some embodiments, the diameter of the shunting component 1430 may be sized to provide shunting of the tissue wall when the balloon element 1400 is in an inflated state (e.g., a first inflated state and/or a second inflated state). In some instances, after the balloon element 1400 is expanded, as shown in FIG. 14, energy (e.g., ablative energy, radiofrequency (RF) energy, phased RF energy, thermal energy, cryogenic energy, pulse ablative energy (e.g., pulsed field ablation (PFA)), microwave energy, laser energy, ultrasound energy, etc.) may be delivered to one or more electrodes disposed on the shunting component 1430 to ablate tissue surrounding the shunting component 1430.

Figure 15:
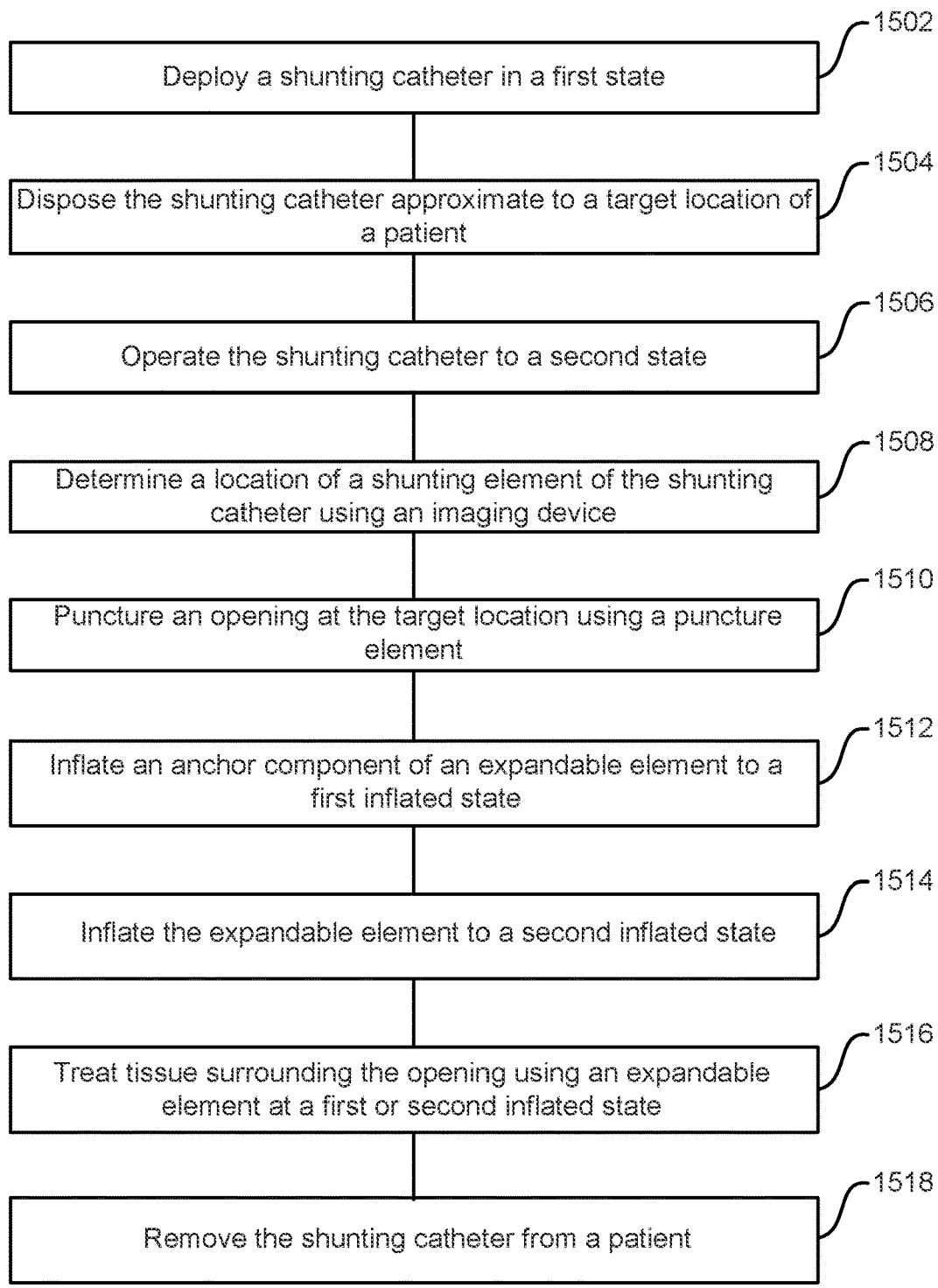
FIG. 15 is a flow diagram illustrating a process of creating a shunt in a patient, in accordance with embodiments of the present disclosure.

FIG. 15 is a flow diagram illustrating a process 1500 of creating a shunt in a patient, in accordance with embodiments of the present disclosure. Aspects of embodiments of the process 1500 may be performed, for example, by a shunting catheter system or a controller (e.g., the system 104 in FIG. 1, the controller 112 in FIG. 1). One or more steps of the process 1500 are optional and/or can be modified by one or more steps of other embodiments described herein. Additionally, one or more steps of other embodiments described herein may be added to the process 1500. In some embodiments, the shunt may be formed in a coronary sinus of a patient. In certain embodiments, the shunt includes an opening between a patient's coronary sinus and left atrium.

At step 1502, in some embodiments, the process 1500 includes deploying a shunting catheter in a first state, the shunting catheter including a catheter shaft having a distal end and a proximal end and a shaft lumen, a shunting element having a proximal end and a distal end, and a puncture element disposed proximate to the distal end of the shunting element. In some embodiments, the shunting element is disposed in the shaft lumen at the first state. In certain embodiments, the catheter shaft has a shaft opening, and the shunting element extends from the catheter shaft through the shaft opening. In certain embodiments, deploying the shunting catheter includes inserting the shunting catheter through a superior vena cava of a patient into a coronary sinus of the patient. In certain embodiments, deploying the shunting catheter includes inserting the shunting catheter through an inferior vena cava of a patient into a coronary sinus of the patient.

At step 1504, the process 1500 includes disposing the shunting catheter approximate to a target location of a patient. At step 1506, the process 1500 includes operating the shunting catheter to a second state, for example, the shunting element extends from the catheter shaft at an angle greater than zero degree at the proximal end of the shunting element at the second state. In some embodiments, the shunting catheter includes an apposition element disposed proximate to the shunting element, and the apposition element is protruded from the catheter shaft at the second state. In certain embodiments, the catheter shaft has a shaft opening, and the shunting element extends from the catheter shaft through the shaft opening.

At step 1508, the process 1500 may include determining a location of the shunting element using an imaging device. In some embodiments, the imaging device includes one or more visualization elements disposed proximate the shunting element.

At step 1510, the process 1500 includes puncturing, using the puncture element, an opening at the target location. In some embodiments, the target location is at a coronary sinus of a patient. In certain embodiments, the shunting catheter includes an expandable element including an anchor component (e.g., the anchor component 1332) and a shunting component (e.g., the shunting component 1330). In some embodiments, the process 1500 includes disposing the anchor component distal of the opening at the target location. At step 1512, the process 1500 includes inflating an anchor component of an expandable element to a first inflated state. In some embodiments, the shunting component remains deflated in the first inflated state. In certain embodiments, the process 1500 includes moving the expandable element in a proximal direction to allow the anchor component to pull back a tissue wall at the target location.

At step 1514, in certain examples, the process 1500 includes inflating the expandable element of the shunting component to a second inflated state. In some examples, the process 1500 includes expanding the opening using the expandable element (e.g., the expandable element 312 in FIG. 3). In certain embodiments, the process 1500 includes expanding the opening using the shunting component of the expandable element.

At step 1516, the process 1500 includes treating tissue (e.g., by ablating, displacing, burning, or shrinking the tissue) surrounding the opening using an expandable element at a first or second inflated state. In some embodiments, the shunting element includes an expandable element (e.g., a balloon) disposed at the distal end of the shunting element. In certain embodiments, the expandable element includes an anchor component and a shunting component (e.g., anchor component 1332 and shunting component 1330). In certain embodiments, each of the anchor component and the shunting component has a plurality of states including a compressed state, a first inflated state, and a second inflated state. In some instances, the shunting component is expanded at the second state and configured to deliver energy (e.g., ablative energy, radiofrequency (RF) energy, phased RF energy, thermal energy, cryogenic energy, pulse ablative energy (e.g., pulsed field ablation (PFA)), microwave energy, laser energy, ultrasound energy, etc.) to the tissue surrounding the opening.

In some embodiments, the expandable element is expanded to an inflated state (a first inflated state and/or a second inflated state) from a compressed state after the puncture element punctures through a tissue wall. The diameter of the anchor component, when expanded to an inflated state, may be substantially larger than the diameter of the puncture hole through the tissue wall, such that as the expandable element is pulled back through the puncture hole, the anchor component is configured to pull back the tissue wall. In some instances, the diameter of the anchor component is large enough to pull back the tissue wall when the anchor component is in the first inflated state. In some instances, the diameter of the anchor component is large enough to pull back the tissue wall when the anchor component is in the second inflated state. The position of the expandable element may be fixed with respect to the tissue wall when the anchor component pulls back the tissue wall.

In some embodiments, the shunting component and the anchor component may share an interior lumen such that both the shunting component and the anchor component are simultaneously inflated. In some embodiments, the shunting component and the anchor component may be separately inflatable balloons. In some instances, the shunting component and the anchor component may not share a lumen, such that the anchor component and the shunting component are inflatable independent of one another.

In certain embodiments, the process 1500 includes disposing the anchor component distal of the opening at the target location, expanding the anchor component to one of a first inflated state or a second inflated state while the shunting component remains in a compressed state, and moving the expandable element in a proximal direction to allow the anchor component to pull back a tissue wall at the target location. In certain embodiments, the process 1500 thereafter includes expanding the shunting component of the expandable element to one of a first inflated state or a second inflated state to expand the opening. In some embodiments, the process 1500 thereafter includes treating tissue (e.g., by ablating, displacing, burning, or shrinking the tissue) surrounding the opening using the shunting component.

At step 1518, the process 1500 may include removing the shunting catheter from a patient. In some embodiments, the process 1500 may include removing the shunting catheter, which includes removing the catheter shaft, the puncture element, and the shunting element. In certain embodiments, the process 1500 does not leave any implant device at the target location. In some embodiments, a shunt is formed by creating an opening between a coronary sinus and a left atrium of a patient. In certain embodiments, the shunting catheter is removed from the coronary sinus of the patient. In certain embodiments, the formed shunt is an opening that does not include an implant (e.g., a frame or structure to support an opening). In some embodiments, the shunt consists of an opening between the coronary sinus and the left atrium of a patient; where the shunt does not include an implant.

According to some embodiments, the process 1500 includes generating a shunt using a shunting element of a shunting catheter. In certain embodiments, the shunt includes an expanded opening between the coronary sinus and left atrium of a patient. In some embodiments, the shunt does not include any implant.

According to one aspect, a shunting catheter includes a catheter shaft having a distal end and a proximal end, the catheter shaft including a shaft lumen; a balloon shaft disposed in the shaft lumen at a first state and extended from the catheter shaft at a second state; a balloon element disposed on the balloon shaft and expandable at the second state; and at least one electrode of one or more electrodes disposed on the balloon element.

According to another aspect, the catheter shaft defines a first axis; wherein the balloon shaft defines a second axis at the second state; wherein the second axis and the first axis form an angle greater than zero degrees.

According to another aspect, the angle is greater than ten degrees.

According to another aspect, the angle is thirty degrees.

According to another aspect, the balloon element has a balloon length along the second axis and a balloon width perpendicular to the second axis; wherein the balloon length is greater than the balloon width when the balloon element is inflated.

According to another aspect, the balloon element has a balloon length along the second axis and a balloon width perpendicular to the second axis; wherein the balloon length is smaller than the balloon width when the balloon element is inflated.

According to another aspect, the balloon element has a diameter in the ranges of three millimeters to fifteen millimeters when the balloon element is inflated.

According to another aspect, the balloon element has a diameter in the ranges of five millimeters to ten millimeters when the balloon element is inflated.

According to another aspect, the balloon element has a first inflated state and a second inflated state; wherein the balloon element has a first balloon diameter at the first inflated state; wherein the balloon element has a second balloon diameter at the second inflated state; wherein the first balloon diameter is different from the second balloon diameter.

According to another aspect, the balloon element includes a first inflatable portion having a first balloon diameter and a second inflatable portion having a second balloon diameter when the balloon element is inflated; wherein the first balloon diameter is different from the second balloon diameter.

According to another aspect, the balloon element includes a narrow section in a middle of the balloon element; wherein the balloon element includes a first section at a distal end of the balloon element and a second section at a proximal end of the balloon element; wherein the narrow section is between the first section and the second section; wherein the narrow section has a diameter smaller than a diameter of the first section or a diameter of the second section.

According to another aspect, the balloon element has a cross-sectional shape perpendicular to the second axis; wherein the cross-section shape is circular, oval or rectangular.

According to one aspect, a shunting catheter system includes: a shunting catheter including: a catheter shaft having a distal end and a proximal end, the catheter shaft including a shaft lumen; a shunting element disposed in the shaft lumen at a first state and extended from the catheter shaft at a second state; and an apposition element disposed proximate to the shunting element, the apposition element being protruded from the catheter shaft at the second state; and an energy source connected to the shunting catheter; and a controller connected to the energy source including one or more processors; wherein the one or more processors are configured to control the energy source to deliver energy to the shunting catheter.

According to another aspect, the shunting catheter system further includes an imaging device including: one or more visualization elements disposed proximate the shunting element for determining a location of the shunting element within a heart of a patient, and a display for visualizing the location.

According to one aspect, a method for creating a shunt includes deploying a shunting catheter in a first state, the shunting catheter including: a catheter shaft having a distal end and a proximal end, the catheter shaft including a shaft lumen; a shunting element having a proximal end and a distal end, wherein the shunting element is disposed in the shaft lumen at the first state; and a puncture element disposed proximate to the distal end of the shunting element; disposing the shunting catheter approximate to a target location of a patient; operating the shunting catheter to a second state, wherein the shunting element extends from the catheter shaft at an angle greater than zero degree at the proximal end of the shunting element at the second state; puncturing, using the puncture element, an opening at the target location; and expanding the opening using the shunting element.

According to another aspect, the shunting element includes an expandable element disposed at the distal end of the shunting element; wherein the expandable element has a plurality of states.

According to another aspect, the plurality of states of the expandable element includes a compressed state, a first inflated state, and a second inflated state.

According to another aspect, the method further includes treating tissue surrounding the opening using the expandable element at the first inflated state.

According to another aspect, the method further includes treating tissue surrounding the opening using the expandable element at the second inflated state.

According to another aspect, the catheter shaft has a shaft opening, wherein the shunting element extends from the catheter shaft through the shaft opening.

According to another aspect, the method further includes determining a location of the shunting element using an imaging device; wherein the imaging device includes one or more visualization elements disposed proximate the shunting element.

According to another aspect, the target location is at a coronary sinus of the patient.

According to another aspect, the method further includes deploying the shunting catheter in the first state includes inserting the shunting catheter through a superior vena cava or an inferior vena cava of the patient into a coronary sinus of the patient.

According to another aspect, the method further includes removing the shunting catheter from the patient.

According to another aspect, the method further includes generating the shunt using the shunting element; wherein the shunt includes the expanded opening between the coronary sinus and a left atrium of the patient.

According to another aspect, the shunt does not include any implant.

According to one aspect, a shunting catheter includes: a catheter shaft having a distal end and a proximal end, the catheter shaft including a shaft lumen; a balloon shaft disposed in the shaft lumen at a first state and extended from the catheter shaft at a second state; a balloon element disposed on the balloon shaft and expandable at the second state; wherein the balloon is configured to deliver energy (e.g., ablative energy, radiofrequency (RF) energy, phased RF energy, thermal energy, cryogenic energy, pulse ablative energy (e.g., pulsed field ablation (PFA)), microwave energy, laser energy, ultrasound energy, etc.) to a target location of a patient.

According to another aspect, the target location is at a coronary sinus of the patient.

According to another aspect, the balloon is configured to expand an opening at the target location.

According to another aspect, the energy source is configured to deliver energy including: ablative energy, radiofrequency (RF) energy, phased RF energy, thermal energy, cryogenic energy, pulse ablative energy (e.g., pulsed field ablation (PFA)), microwave energy, laser ablative energy, or ultrasound energy.

According to another aspect, the treating tissue surrounding the opening includes ablating, displacing, burning, or shrinking the tissue surrounding the opening.

According to another aspect, the balloon element includes: an anchor component configured to facilitate a placement of the balloon element within a patient; and a shunting component mechanically coupled to the anchor component.

According to another aspect, the anchor component has a first diameter, wherein the shunting component has a second diameter, and wherein the first diameter is larger than the second diameter.

According to another aspect, the at least one electrode of the one or more electrodes is disposed on the shunting component of the balloon element.

According to another aspect, the anchor component and the shunting component share an interior lumen.

According to another aspect, the anchor component is a first balloon and the shunting component is a second balloon that does not share lumen with the first balloon.

According to another aspect, the anchor component is configured to be inflated to a first inflated state and the shunting component is configured to remain deflated at the first inflated state, wherein the anchor component is configured to be inflated to a second inflated state and the shunting component is configured to remain deflated at the second inflated state.

According to another aspect, the anchor component is configured to pull back a tissue wall at the first inflated state.

According to another aspect, the shunting component has a diameter in the ranges of 2 millimeters to 12 millimeters at the second inflated state.

According to another aspect, the anchor portion has a diameter in the ranges of 4 millimeters to 16 millimeters at the second inflated state.

According to another aspect, the balloon element is folded into a plurality of pleats at the first state, and wherein a first electrode of the one or more electrodes is disposed entirely on a pleating surface on one side of one of the plurality of pleats.

According to another aspect, the at least one electrode of the one or more electrodes has a longitudinal center portion and a plurality of protrusions extended from the center portion, wherein at least a part of the plurality of protrusions are parallel.

According to another aspect, the anchor component has a proximal surface defining a plane perpendicular to a longitudinal axis of the balloon element.

According to another aspect, the anchor component has a proximal surface forming an angle less than 90 degrees relative to a longitudinal axis of the balloon element.

According to another aspect, the anchor component has a proximal surface forming an angle more than 90 degrees relative to a longitudinal axis of the balloon element.

According to another aspect, the anchor component has a canted shape such that a first portion of a proximal surface of the anchor component forms an acute angle relative to a longitudinal axis of the balloon element, and a second portion of the proximal surface of the anchor component forms an obtuse angle relative to the longitudinal axis of the balloon element.

According to another aspect, the target location is at an atrial septum of the patient.

According to another aspect, the shunting element includes an expandable element disposed at the distal end of the shunting element, wherein the expandable element includes an anchor component, wherein the anchor component has a plurality of states including a compressed state, a first inflated state, and a second inflated state, wherein the method includes: expanding the anchor component to one of the first inflated state or the second inflated state when the anchor component is disposed distal of the target location; moving the shunting element in a proximal direction to allow the anchor component to pull back a tissue wall at the target location.

Various modifications and additions can be made to the exemplary embodiments discussed without departing from the scope of the present disclosure. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. A shunting catheter, comprising:
   a catheter shaft having a distal end and a proximal end, the catheter shaft including a shaft lumen;
   a balloon shaft disposed in the shaft lumen at a first state and extended from the catheter shaft at a second state;
   a balloon element disposed on the balloon shaft and expandable at the second state; and
   at least one electrode of one or more electrodes disposed on the balloon element;
   wherein the balloon element includes a plurality of pleats at the first state;
   wherein a first pleat of the plurality of pleats comprises a first pleating surface on a first side of the first pleat and a second pleating surface on a second side of the first pleat;

wherein the second side is opposing to the first side;
wherein a first electrode of the one or more electrodes is disposed entirely on the first pleating surface at the first state;
wherein a second electrode of the one or more electrodes is disposed entirely on the second pleating surface at the first state.

2. The shunting catheter of claim 1, wherein the catheter shaft defines a first axis; wherein the balloon shaft defines a second axis at the second state; wherein the second axis and the first axis form an angle greater than zero degrees.

3. The shunting catheter of claim 2, wherein the balloon element has a balloon length along the second axis and a balloon width perpendicular to the second axis; wherein the balloon length is greater than the balloon width when the balloon element is inflated.

4. The shunting catheter of claim 2, wherein the balloon element has a balloon length along the second axis and a balloon width perpendicular to the second axis; wherein the balloon length is smaller than the balloon width when the balloon element is inflated.

5. The shunting catheter of claim 2, wherein the balloon element has a cross-sectional shape perpendicular to the second axis; wherein the cross-section shape is circular, oval or rectangular.

6. The shunting catheter of claim 1, wherein the balloon element has a diameter in a range of three millimeters to fifteen millimeters when the balloon element is inflated.

7. The shunting catheter of claim 1, wherein the balloon element has a first inflated state and a second inflated state; wherein the balloon element has a first balloon diameter at the first inflated state; wherein the balloon element has a second balloon diameter at the second inflated state; wherein the first balloon diameter is different from the second balloon diameter.

8. The shunting catheter of claim 1, wherein the balloon element includes a first inflatable portion having a first balloon diameter and a second inflatable portion having a second balloon diameter when the balloon element is inflated; wherein the first balloon diameter is different from the second balloon diameter.

9. The shunting catheter of claim 1, wherein the balloon element includes a narrow section in a middle of the balloon element; wherein the balloon element includes a first section at a distal end of the balloon element and a second section at a proximal end of the balloon element; wherein the narrow section is between the first section and the second section; wherein the narrow section has a diameter smaller than a diameter of the first section or a diameter of the second section.

10. The shunting catheter of claim 1, wherein the balloon element comprises:
an anchor component configured to facilitate a placement of the balloon element within a patient; and
a shunting component mechanically coupled to the anchor component.

11. The shunting catheter of claim 10, wherein the anchor component has a first diameter at the second state, wherein the shunting component has a second diameter at the second state, and wherein the first diameter is larger than the second diameter.

12. The shunting catheter of claim 10, wherein the at least one electrode of the one or more electrodes is disposed on the shunting component of the balloon element.

13. The shunting catheter of claim 10, wherein the anchor component and the shunting component share an interior lumen.

14. The shunting catheter of claim 10, wherein the anchor component is a first balloon and the shunting component is a second balloon that does not share lumen with the first balloon.

15. The shunting catheter of claim 10, wherein the anchor component is configured to be inflated at a first inflated state and the shunting component is configured to remain deflated at the first inflated state, wherein the anchor component is configured to remain inflated at a second inflated state and the shunting component is configured to be inflated at the second inflated state.

16. The shunting catheter of claim 10, wherein the anchor component is configured to pull back a tissue wall at a first inflated state.

17. The shunting catheter of claim 10, wherein the anchor component has a proximal surface defining a plane angled relative to a longitudinal axis of the balloon element at the second state.

18. The shunting catheter of claim 1, wherein the at least one electrode of the one or more electrodes has a center portion and a plurality of protrusions extended from the center portion, wherein at least a part of the plurality of protrusions are parallel.

19. The shunting catheter of claim 1, wherein the first electrode extends generally parallel to the balloon shaft at the first state.

20. The shunting catheter of claim 1, wherein the at least one electrode of one or more electrodes includes a grid pattern.

21. A shunting catheter, comprising:
a catheter shaft having a distal end and a proximal end, the catheter shaft including a shaft lumen;
a balloon shaft disposed in the shaft lumen at a first state and extended from the catheter shaft at a second state;
a balloon element disposed on the balloon shaft and configured to be expandable at the second state; and
at least one electrode of one or more electrodes disposed on the balloon element;
wherein the balloon element includes an anchor component and a shunting component, the anchor component is configured to position the balloon element at a target location of a patient, and the shunting component has a diameter smaller than a diameter of the anchor component when both the anchor component and the shunting component are inflated;
wherein the shunting component is configured to deliver ablation energy to the target location of the patient,
wherein the balloon element includes a plurality of pleats at the first state;
wherein a first pleat of the plurality of pleats comprises a first pleating surface on a first side of the first pleat and a second pleating surface on a second side of the first pleat;
wherein the second side is opposing to the first side;
wherein a first electrode of the one or more electrodes is disposed entirely on the first pleating surface at the first state;
wherein a second electrode of the one or more electrodes is disposed entirely on the second pleating surface at the first state.

* * * * *